United States Patent
Pack et al.

(10) Patent No.: US 7,477,720 B2
(45) Date of Patent: Jan. 13, 2009

(54) CONE-BEAM RECONSTRUCTION USING BACKPROJECTION OF LOCALLY FILTERED PROJECTIONS AND X-RAY CT APPARATUS

(75) Inventors: Jed Douglas Pack, Schenectady, NY (US); Frédéric Noo, Midvale, UT (US); Rolf Clackdoyle, Chamboeuf (FR)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 11/371,718

(22) Filed: Mar. 9, 2006

(65) Prior Publication Data
US 2006/0291611 A1    Dec. 28, 2006

Related U.S. Application Data

(60) Provisional application No. 60/694,652, filed on Jun. 28, 2005.

(51) Int. Cl.
*A61B 6/03* (2006.01)
(52) U.S. Cl. .......................................... 378/4; 382/131
(58) Field of Classification Search ............... 378/4, 378/19, 201, 901; 382/128–131
See application file for complete search history.

(56) References Cited

U.S. PATENT DOCUMENTS

| | | | | |
|---|---|---|---|---|
| 4,888,693 | A * | 12/1989 | Tam ............................. | 378/4 |
| 6,018,561 | A | 1/2000 | Tam | |
| 6,097,784 | A | 8/2000 | Tuy | |
| 6,574,299 | B1 | 6/2003 | Katsevich | |
| 6,865,247 | B2 | 3/2005 | Hagiwara | |
| 6,947,584 | B1 * | 9/2005 | Avila et al. .................. | 382/131 |
| 2003/0202637 | A1 | 10/2003 | Yang | |
| 2004/0156469 | A1 | 8/2004 | Nishide et al. | |
| 2005/0249432 | A1 * | 11/2005 | Zou et al. .................... | 382/276 |
| 2006/0050842 | A1 * | 3/2006 | Wang et al. .................. | 378/16 |
| 2006/0109952 | A1 * | 5/2006 | Chen ............................ | 378/4 |
| 2006/0140335 | A1 * | 6/2006 | Heuscher et al. ............. | 378/4 |

FOREIGN PATENT DOCUMENTS

| | | | |
|---|---|---|---|
| WO | WO 2004/072904 A1 | | 8/2004 |
| WO | WO2007004196 A2 * | | 1/2007 |

OTHER PUBLICATIONS

Kudo et al. (Phys. Med. Biol. 49 (2004) 2913-2931).*
Noo et al., A two-step Hilbert transformation method for 2D image reconstruction, Aug. 6, 2994, Phys. Med. Biol. vol. 49, pp. 3903-3923.*
Zou et al., Exact image reconstruction on PI-lines from minimum data in helical cone-beam CT, Feb. 24, 2004, Phys. Med. Biol., vol. 49, pp. 941-959.*

(Continued)

*Primary Examiner*—Chih-Cheng G Kao
*Assistant Examiner*—John M Corbett
(74) *Attorney, Agent, or Firm*—Morriss O'Bryant Compagni

(57) ABSTRACT

Embodiments of the present invention include a method and apparatus for accurate cone beam reconstruction with source positions on a curve (or set of curves). The inversion formulas employed by embodiments of the method of the present invention are based on first backprojecting a simple derivative in the projection space and then applying a Hilbert transform inversion in the image space.

14 Claims, 12 Drawing Sheets

OTHER PUBLICATIONS

Zou et al., Image reconstruction on PI-lines by use of filtered backprojection in helical cone-beam CT, Jun. 4, 2004, Phys. Med. Biol. vol. 49, pp. 2717-2731.*

Ye et al., Exact reconstruction for cone-beam scanning along non-standard spirals and other curves, Developments in X-Ray Tomography IV, Aug. 4-6, 2004, SPIE vol. 5535, pp. 293-300.*

Zhao et al., A Family of Analytic Algorithms for Cone-Beam CT, Developments in X-Ray Tomography IV, Aug. 4-6, 2004, SPIE vol. 5535, pp. 318-328.*

Pack et al., Investigation of saddle trajectories for cardiac CT imaging in cone-beam geometry, May 19, 2004, Phys. Med. Biol., vol. 49, pp. 2317-2336.*

Zou et al., Image reconstruction in regions-of-interest from truncated projections in a reduced fan-beam scan, Dec. 16, 2004, Phys. Med. Biol., vol. 50, pp. 13-27.*

"Direct Reconstruction of Cone-Beam Data Acquired with a Vertex Path Containing a Circle". Frédéric Noo, Michel Defrise, Rolf Clack. IEEE Transactions on Image Processing, vol. 7, No. 6, 854-867. Jun. 1998.

"Feldkamp and circle-and-line cone-beam reconstruction for 3D micro-CT of vascular networks". Roger H. Johnson, Hui Hu, Steven T. Haworth, Paul S. Cho, Christopher A. Dawson, John H. Linehan. Phys. Med. Biol. 43 (1998) 929-940.

"Fast and stable cone-beam filtered backprojection method for non-planar orbits". Hiroyuki Kudo, Tsuneo Saito. Phys. Med. Biol. 43 (1998) 747-760.

"Quasi-Exact Filtered Backprojection Algorithm for Long-Object Problem in Helical Cone-Beam Tomography". Hiroyuki Kudo, Frédéric Noo, Michel Defrise. IEEE Transactions on Medical Imaging, vol. 19, No. 9, 902-921. Sep. 2000.

"Exact local regions-of-interest reconstruction in spiral cone-beam filtered-backprojection CT: numerical implementation and first image results". Günter Lauritsch, Kwok C. Tam, Katia Sourbelle, Stefan Schaller. Medical Imaging 2000: Image Processing, Kenneth M. Hanson, Editor, Proceedings of SPIE vol. 3979, 520-532, (2000).

"Filtering point spread function in backprojection cone-beam CT and its applications in long object imaging". K. C. Tam, G. Lauritsch, K. Sourbelle. Phys. Med. Biol. 47 (2002) 2685-2703.

"A General Scheme for Constructing Inversion Algorithms for Cone Beam CT". Alexander Katsevich. IJMMS 2003:21, 1305-1321.

"An alternative derivation of Katsevich's cone-beam reconstrution formula". Guang-Hong Chen. Med. Phys. 30 (12), Dec. 2003, 3217-3226.

"Investigation of saddle trajectories for cardiac CT imaging in cone-beam geometry". Jed D. Pack, Frédéric Noo, H. Kudo. Phys. Med. Biol. 49 (2004) 2317-2336.

"Cone-beam filtered-backprojection algorithm for truncated helical data". Hiroyuki Kudo, Frédéric Noo, Michel Defrise. Phys. Med. Biol. 43 (1998) 2885-2909.

"Exact cone beam CT with a spiral scan". K. C. Tam, S. Samarasekera, F. Sauer. Phys. Med. Biol. 43 (1998) 1015-1024.

"Exact Radon Rebinning Algorithm for the Long Object Problem in Helical Cone-Beam CT". S. Schaller, F. Noo, F. Sauer, K.C. Tam, G. Lauritsch, T. Flohr. IEEE Transactions on Medical Imaging, vol. 19, No. 5, May 2000, 361-375.

"A cone beam filtered backprojection (CB-FBP) reconstruction algorithm for a circle-plus-two-arc orbit". Xiangyang Tang, Ruola Ning. Med. Phys. 28 (6), Jun. 2001. 1042-1055.

"An improved exact filtered backprojection algorithm for spiral computed tomography". Alexander Katsevich.

"Exact image reconstruction on PI-lines from minimum data in helical cone-beam CT". Yu Zou, Xiaochuan Pan. Phys. Med. Biol. 49 (2004) 941-959.

"Practical cone-beam algorithm". L. A. Feldkamp, L. C. Davis, J. W. Kress. J. Opt. Soc. Am. A / vol. 1, No. 6 / Jun. 1984. 612-619.

"A two-step Hilbert transform method for 2D image reconstruction". Frédéric Noo, Rolf Clackdoyle, Jed D. Pack. Phys. Med. Biol. 49 (2004) 3903-3923.

"Exact helical reconstruction using native cone-beam geometries". Frédéric Noo, Jed Pack, Dominic Heuscher. Phys. Med. Biol. 48 (2003) 3787-3818.

"The n-PI-Method for Helical Cone-Beam CT". R. Proska, Th. Köhler, M. Grass, J. Timmer. IEEE Transactions on Medical Imaging, vol. 19, No. 9, Sep. 2000. 848-863.

"Redundant data and exact helical cone-beam reconstruction". D. Heuscher, K. Brown, F. Noo. Phys. Med. Biol. 49 (2004) 2219-2238.

"Image reconstruction and image quality evaluation for a 16-slice CT scanner". Th. Flohr, K. Stierstorfer, H. Bruder, J. Simon, A. Polacin, S. Schaller. Med. Phys. 30 (5), May 2003. 832-845.

"An Extended Completeness Condition for Exact Cone-Beam Reconstruction and Its Application". Hiroyuki Kudo, Tsuneo Saito.

"Extended Cone-Beam Reconstruction Using Radon Transform". Hiroyuki Kudo, Tsuneo Saito.

"Reconstruction from ray integrals with sources on a curve". V. P. Palamodov. Inverse Problems 20 (2004) 239-242.

\* cited by examiner

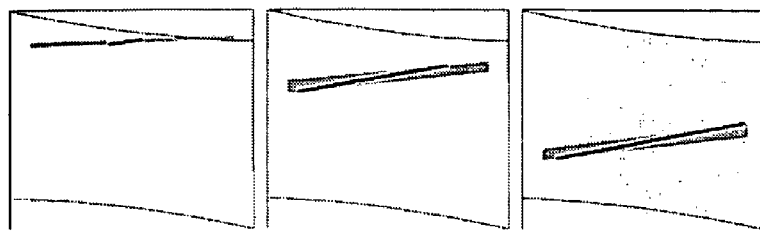
FIG. 5
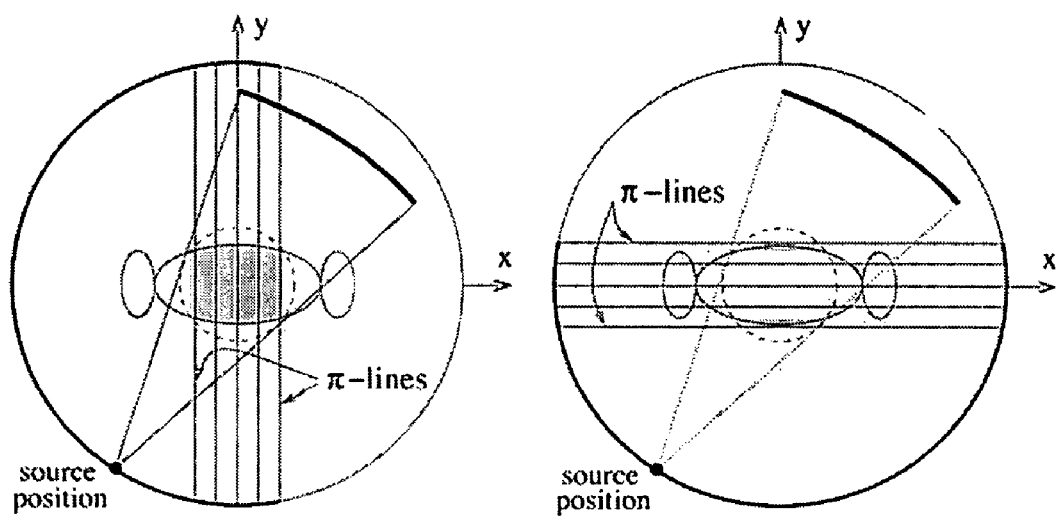
FIG. 6A          FIG. 6B

CONE-BEAM RECONSTRUCTION USING BACKPROJECTION OF LOCALLY FILTERED PROJECTIONS AND X-RAY CT APPARATUS

CROSS-REFERENCE TO RELATED APPLICATIONS

This nonprovisional patent application claims benefit and priority under 35 U.S.C. § 119(e) of the filing of U.S. Provisional Patent Application Ser. No. 60/694,652 filed on Jun. 28, 2005, titled "CONE-BEAM RECONSTRUCTION," the contents of which are incorporated herein by reference for all purposes.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for in the terms of grants R21 EB000568 and R01 EB000621 awarded by the U.S. Department of Health and Human Services, National Institutes of Health (NIH).

BACKGROUND OF THE INVENTION

1. Field of the Invention

This invention relates generally to reconstruction of the density function of a three-dimensional object from a set of cone-beam projections, such as from an X-ray source. More particularly, the invention relates to methods for cone beam reconstruction using backprojection of locally filtered projections and an X-ray computed tomography (CT) apparatus incorporating the method.

2. Description of Related Art

Technology for X-ray detection in cone-beam (CB) geometry is rapidly improving and offers more and more potential for the construction of robust computed tomography (CT) systems for fast high-resolution volume imaging. However, to optimally build such systems, the problem of CB image reconstruction needs to be fully understood.

The successive works of H. Tuy, "An Inversion Formula for Cone-Beam Reconstruction," *SIAM J. Appl. Math.*, No. 43, pp. 546-52, 1983, B. D. Smith, "Image Reconstruction from Cone-Beam Projections: Necessary and Sufficient Conditions and Reconstruction Methods," *IEEE Trans. Med. Imag.*, Vol. MI-4, pp. 1425, 1985 and P. Grangeat, "Mathematical Framework of Cone-Beam 3D Reconstruction via the First Derivative of the Radon Transform," in *Mathematical Methods in Tomography*, G. T. Herman, A. K, Louis, and F. Natterer, Eds. Berlin, Germany: Springer-Verlag, 1991, Vol. 1497, Lecture Notes in Mathematics, pp. 66-97, have shown that exact reconstruction at a given location is possible if every plane passing through that location intersects the trajectory of the X-ray source. However, this well-known result, which is fundamental and clearly represented a breakthrough, is not sufficient for most practical applications because its derivation assumed complete CB projections. When only part of the imaged object is illuminated at a given source position, the CB projection is said to be incomplete or truncated. Exact and accurate reconstruction from truncated projections is more complicated than from complete projections. An overview of the problem of reconstructing from truncated projections may be found in R. Clackdoyle, M. Defrise and F. Noo, "Early Results on General Vertex Sets and Truncated Projections in Cone-Beam Tomography," in *Computational Radiology and Imaging: Therapy and Diagnostics*, C. Brgers and F. Natterer, Eds. Berlin, Germany: Springer-Verlag, 1999, Vol. 110, IMA Volumes in Mathematics and Its Applications, pp. 113-135. Under some conditions, the problem of reconstructing from truncated projections may even be impossible, see e.g., F. Natterer, *The Mathematics of CT*, Philadelphia, Pa.: SIAM, 2001.

A general theory to handle CB data truncation remains elusive. Solutions have been found only for particular measurement geometries. Many of these solutions were obtained using a clever handling of data redundancy in a CB filtered-backprojection (FBP) reconstruction framework. See e.g., H. Kudo and T. Saito, "An Extended Completeness Condition for Exact Cone-Beam Reconstruction and Its Applications," in *Conf. Rec. 1994 IEEE Nuclear Science Symp. Medical Imaging Conf.*, Norfolk Va., 1995, pp. 1710-14; F. Noo, R. Clackdoyle, and M. Defrise, "Direct Reconstruction of Cone-Beam Data Acquired with a Vertex Path Containing a Circle," *IEEE Trans, Image Process.*, Vol. 7, No. 6, pp. 854-67, Jun. 1998; R. H. Johnson, H. Hu, S. T. Haworth, P. S. Cho, C. A. Dawson and J. H. Linehan, "Feldkamp and Circle and Line Cone-Beam Reconstruction for 3D Micro-CT of Vascular Networks," *Phys. Med. Biol.* Vol. 43, pp. 929-40, 1998; H. Kudo and T. Saito, "Fast and Stable Cone-Beam Filtered Backprojection Method for Nonplanar Orbits," *Phys. Med. Biol.*, Vol. 43, pp. 747-60, 1998; H. Kudo, F. Noo and M. Defrise, "Quasi-Exact Filtered Backprojection Algorithm for Long-Object Problem in Helical Cone-Beam Tomography," *IEEE Trans, Med. Imag.*, Vil. 19, No. 9, pp. 902-21, September 2000; G. Lauritsch, K. C. Tam, K. Sourbelle and S. Schaller, "Exact Local Region-of-Interest Reconstruction in Spiral Cone-Beam Filtered-Backprojection CT: Numerical Implementation and First Image Results," in *Proc. SPIE Medical Imaging Conf. (Image Processing)*, Vol. 3979, 2000, pp. 520-32; K. C. Tam, G. Lauritsch and K. Sourbelle, "Filtering Point Spread Function in Backprojection Cone-Beam CT and Its Applications in Long Object Imaging," *Phys, Med. Biol.*, Vol. 47, pp. 2685-703, 2002; A. Katesevich, "A General Scheme for Constructing Inversion Algorithms for Cone-Beam CT," *I.J.M.M.S.*, Vol. 21, pp. 1305-21, 2003; G. H. Chen, "An Alternative Derivation of Katsevich's Cone-Beam Reconstruction Formula," *Med. Phys.*, Vol. 30, No. 12, pp. 3217-26, 2003; J. D. Pack, F. Noo and H. Kudo, "Investigation of Saddle Trajectories for Cardiac CT Imaging in Cone-Beam Geometry," *Phys. Med. Biol.*, Vol. 49, No. 11, pp. 2317-36; and H. Kudo, F. Noo and M. Defrise, "Cone-Beam Filtered-Backprojection Algorithm for Truncated Helical Data," *Phys. Med. Biol.*, Vol. 43, pp. 2885-909, 1998.

Other solutions for CB reconstruction from truncated projections for particular measurement geometries were obtained using the formula posed by Grangeat or its truncated version, see H. Kudo, F. Noo, and M. Defrise, "Cone-Beam Filtered-Backprojection Algorithm for Truncated Helical Data," Phys. Med. Biol., Vol. 43, pp. 2885-909, 1998, in combination with properties of the three-dimensional (3-D) radon transform. See, e.g., H. Kudo and T. Saito, "Extended Cone-Beam Reconstruction Using Radon Transform," in *Conf Rec. 1996 IEEE Nuclear Science Symp. Medical Imaging Conf.*, Anaheim, Calif., 1997, pp. 1693-97; K. C. Tam, S. Samarasekera and F. Sauer, "Exact Cone-Beam CT with a Spiral Scan," *Phys. Med. Biol*, Vol. 43, pp. 1015-24, 1998; S. Schaller, F. Noo, F. Sauer, K. C. Tam, G. Lauritsch and T. Flohr, "Exact Radon Rebinning Algorithm for the Long Object Problem in Helical Cone-Beam CT," *IEEE Trans, Med. Imag.*, Vol. 19, No. 5, pp. 36 1-75, May 2000; and X. Tang and R. Ning, "A Cone Beam Filtered Backprojection (CB-FBP) Reconstruction Algorithm for a Circle-Plus-Two-Arc Orbit," *Med. Phys.*, Vol. 28, No. 6, pp. 1042-55, 2001.

Many advances in CB reconstruction have been made recently in reconstruction methods for use in helical CB tomography (HCBT). Two of the most interesting results achieved in the HCBT context are disclosed in A. I. Katsevich, "An Improved Exact Filtered Backprojection Algorithm for Spiral Computed Tomography," *Adv. Appl. Math.*, Vol. 32, No. 4, pp. 681-97, 2004 and Y. Zou and X. Pan, "Exact Image Reconstruction on PI Lines from Minimum Data in Helical Cone-Beam CT," *Phys. Med. Biol.*, Vol. 49, pp. 941-59, 2004.

Katsevich showed that exact and accurate FBP reconstruction can be achieved with a simple one-dimensional (1-D) Hilbert transform of a derivative of the projection, using a minimum overscan and just slightly more than the data in the Tam-Danielsson (TD) window, see e.g., K. C. Tam, S. Samarasekera and F. Sauer, "Exact Cone-Beam CT with a Spiral Scan," *Phys. Med. Biol*, Vol. 43, pp. 1015-24, 1998; and P. E. Danielsson, P. Edholm, J. Eriksson and M. Magnusson Seger, "Toward Exact Reconstruction for Helical Cone-Beam Scanning of Long Objects: A New Detector Arrangement and a New Completeness Condition," in *Proc. 1997 Meeting Fully 3D Image Reconstruction in Radiology and Nuclear Medicine*, D. W. Townsend and P. E. Kinahan, Eds., Pittsburgh, Pa., 1997, pp. 141-44. Katsevich has also generalized his formula to general CB tomography and showed incidentally that his formula belongs to the family of methods that can be obtained using a clever handling of data redundancy in a CB-FBP reconstruction framework, see e.g., A. Katesevich, "A General Scheme for Constructing Inversion Algorithms for Cone-Beam CT," *I.J.M.M.S.*, Vol. 21, pp. 1305-21, 2003.

Zou and Pan investigated the effect of skipping the 1-D Hilbert transform in the reconstruction steps of Katsevich's formula. They argued that by so doing the outcome of the backprojection on any $\pi$-line is the Hilbert transform of the values of the density function, $f$, on this $\pi$-line, and they devised from this argument and information on the support of $f$ an accurate algorithm that has the same overscan and efficiency as Katsevich's formula but uses only the data in the TD window. Recall that a $\pi$-line is any line segment that connects two points of the helix separated by less than one helix turn, see e.g., P. E. Danielsson, P. Edholm, J. Eriksson and M. Magnusson Seger, "Toward Exact Reconstruction for Helical Cone-Beam Scanning of Long Objects. A New Detector Arrangement and a New Completeness Condition," in *Proc. 1997 Meeting Fully 3D Image Reconstruction in Radiology and Nuclear Medicine*, D. W. Townsend and P. E. Kinahan, Eds., Pittsburgh, Pa., 1997, pp. 141-44.

None of these conventional approaches appears to achieve CB reconstruction on various measured lines using virtually arbitrary source trajectories. A measured line is any line that contains a source position and is part of the measurements. Thus, it would be highly advantageous to provide a method for CB reconstruction using backprojection of locally filtered projections and an X-ray CT apparatus incorporating such a method.

SUMMARY OF THE INVENTION

Embodiments of the present invention achieve reconstruction on various measured lines (M-lines) using (almost) arbitrary source trajectories. Embodiments of the present invention include applying the processing steps of the well-known algorithm disclosed in L. A. Feldkamp, L. C. Davis and J. W. Kress, "Practical Cone-Beam Algorithm," *J. Opt. Soc. Am. A*, Vol. 1, pp. 612-19, 1984, to segments of source trajectories using a simple derivative along the detector rows instead of the ramp filter and obtain a portion of the Hilbert transform of $f$ on various measured lines. Embodiments of the present invention further include achieving the reconstruction of $f$ on these measured lines by obtaining a 1-D function from its Hilbert transform when the latter is only known over the region where the 1-D function is nonzero.

An embodiment of a method to obtain $f$ on line segments that connect two source positions is disclosed according to the present invention. Such line segments are referred to herein as R-lines, which is a short-hand notation for redundantly measured lines. When the X-ray source trajectory is a helix and the extremities of the R-line are separated by less than one helix turn, the R-line is a $\pi$-line. In general, there is no guarantee for a voxel to belong to an R-line, so the methods of the present invention do not allow reconstruction at arbitrary locations. The locations where reconstruction is achievable is dependent on the source trajectory and the extent of the detector. Fortunately, a large number of data acquisition geometries have their field-of-view (FOV) entirely covered by R-lines, see, e.g., Danielsson et al. for the helix and Pack et al. for the class of saddle trajectories. To the inventors' knowledge, CB image reconstruction on R-lines of general source trajectories was first suggested by Palamodov, who developed a three-term convolution-based FBP formula, see, e.g., V. P. Palamodov, "Reconstruction from Ray Integrals with Sources on a Curve," *Inv. Prob.*, Vol. 20, pp. 239-42, 2004. However, the methods of the present invention require less data than Palamodov's for reconstruction on an R-line and can accommodate a certain degree of transverse data truncation (in addition to axial truncation) for reconstruction on some surfaces of R-lines in the case of the helix or a saddle trajectory.

Another embodiment of a method to compute $f$ on some of the measured lines that have only one intersection with the source trajectory is disclosed according to the present invention. This method offers more flexibility in the design of reconstruction algorithms. In the HCBT context, the method enables transverse truncation to be handled over a much larger region than that allowed by the R-lines approach and also offers a way to incorporate redundant data into the reconstruction process for possible reduction of image noise.

Additional features and advantages of the invention will be apparent from the detailed description which follows, taken in conjunction with the accompanying drawings, which together illustrate, by way of example, features of embodiments of the present invention.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 5 illustrates representations of a detector at three source positions between the endpoints of a central π-line L on a helix according to embodiments of the present invention.

FIGS. 6A and 6B illustrate axial views of a single-turn helical scan of a patient that extends beyond the FOV (dashed circle) in the x-direction according to embodiments of the present invention.

DETAILED DESCRIPTION

This detailed description describes a flexible new methodology for accurate cone-beam reconstruction with source positions on a curve (or set of curves). Embodiments of the methods disclosed herein include inversion formulas that are based on first backprojecting a simple derivative in the projection space and then applying a Hilbert transform inversion in the image space. The local nature of the projection space filtering distinguishes this approach from conventional filtered-backprojection methods. This characteristic together with a degree of flexibility in choosing the direction of the Hilbert transform used for inversion offers two important features for the design of data acquisition geometries, reconstruction algorithms and apparatuses employing the methods of the present invention. First, the size of the detector necessary to acquire sufficient data for accurate reconstruction of a given region is often smaller than that required by previously documented approaches. In other words, more data truncation is allowed. Second, redundant data can be incorporated for the purpose of noise reduction. The validity of the inversion formulas along with the application of these two properties are illustrated with reconstructions from computer simulated data as disclosed herein. In particular, with reference to the helical cone beam geometry context, it is shown that 1) intermittent transaxial truncation has no effect on the reconstruction in a central region, which means that wider patients can be accommodated on existing scanners and, more importantly, that radiation exposure can be reduced for region of interest imaging and, 2) at maximum pitch the data outside the Tam-Danielsson window can be used to reduce image noise and thereby improve dose utilization. Furthermore, the degree of axial truncation tolerated by our approach for saddle trajectories is shown to be larger than that of previous methods.

The following disclosure defines the Hilbert transform of a 3-D object density function on a line in space, and discusses how this transform can be inverted while being only known on the segment of the line where $f$ is nonzero. As will be seen in the next sections, the definitions and results presented here provide the foundations for a versatile theory for image reconstruction from CB projections.

Figure 1:
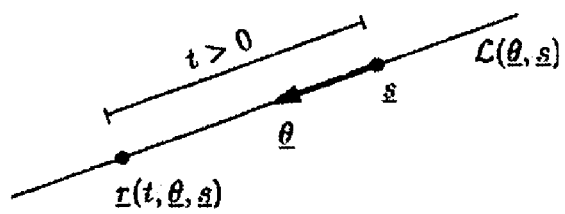
FIG. 1 is an illustration of the line L($\underline{\theta}$,$\underline{s}$) and the point $\underline{r}$(t, $\underline{\theta}$,$\underline{s}$) that is on the line L($\underline{\theta}$,$\underline{s}$) at signed distance t from $\underline{s}$ according to an embodiment of the present invention.

FIG. 1 is an illustration of the line $L(\underline{\theta},\underline{s})$ and the point $\underline{r}(t,\underline{\theta},\underline{s})$ that is on it at signed distance t from $\underline{s}$. Throughout this disclosure, the density function to be reconstructed is either denoted as $f$, $f(x,y,z)$, or $f(\underline{x})$ with $\underline{x}=(x,y,z)$. Also, the support of $f$, which is the smallest closed set enclosing the region where $f$ is nonzero, is denoted $\Omega$. For all developments, it is assumed that $\Omega$ is compact (closed and bounded). Furthermore, it is assumed that $f \geq 0$ like any density function and $f$ is continuously differentiable everywhere, which implies that $f(\underline{x})$ tends to zero when $\underline{x}$ tends toward the boundary of $\Omega$.

Let $\underline{\theta}$ be a unit vector and $\underline{s}$ be a point in space. Then let $L(\underline{\theta},\underline{s})$ be the line of direction $\underline{\theta}$ through $\underline{s}$, and let $$r(t,\underline{\theta},\underline{s})=\underline{s}+t\underline{\theta} \quad (1)$$

be a parameterization of the points on this line, with $t \in (-\infty,+\infty)$, see FIG. 1. Depending on its position and the location and shape of $\Omega$, $L(\underline{\theta},\underline{s})$ may or may not hit $\Omega$. Also, the intersection of $L(\underline{\theta},\underline{s})$ with $\Omega$ may be more than a single line segment when $L(\underline{\theta},\underline{s})$ hits $\Omega$ because $\Omega$ need not be convex. However, the convex hull of the intersection of $L(\underline{\theta},\underline{s})$ and $\Omega$ is always a single line segment when $L(\underline{\theta},\underline{s})$ hits $\Omega$. This line segment corresponds to an interval of t values that is often used in herein and is denoted as region $[t_{min}(\underline{\theta},\underline{s}),t_{max}(\underline{\theta},\underline{s})]$, or more simply as region $[t_{min},t_{max}]$, keeping in mind that $t_{min}$ and $t_{max}$ both depend on $\underline{\theta}$ and $\underline{s}$. By definition, $f$ is zero at any position $\underline{r}(t,\underline{\theta},\underline{s})$ defined with $t \notin (t_{min},t_{max})$, and $t_{min}$ and $t_{max}$ are both finite numbers since $\Omega$ is bounded. Moreover, note that the convex hull of the intersection of $L(\underline{\theta},\underline{s})$ with $\Omega$ is in general smaller than the intersection of $L(\underline{\theta},\underline{s})$ with the convex hull of $\Omega$.

Now let $$k(t,\underline{\theta},\underline{s}) = f(\underline{r}(t,\underline{\theta},\underline{s})) \quad (2)$$

be the function that assigns to any given $t \in (-\infty, +\infty)$ the value of $f$ at location $\underline{r}(t,\underline{\theta},\underline{s})$ on $L(\underline{\theta},\underline{s})$. We define the Hilbert transform of $f$ on the line $L(\underline{\theta},\underline{s})$ as the Hilbert transform of $k(t,\underline{\theta},\underline{s})$ in $t$, namely $$K(t, \underline{\theta}, \underline{s}) = \int_{-\infty}^{\infty} \frac{1}{\pi(t-t')} k(t', \underline{\theta}, \underline{s}) dt' \quad (3)$$

where the singularity at $t'=t$ is handled in the Cauchy Principal Value sense.

By definition, the behavior of $K(t,\underline{\theta},\underline{s})$ depends on the position of $L(\underline{\theta},\underline{s})$ in space. If $L(\underline{\theta},\underline{s})$ has no intersection with $\Omega$, $K(t,\underline{\theta},\underline{s})=0$ everywhere. On the other hand, if $L(\underline{\theta},\underline{s})$ intersects $\Omega$, $K(t,\underline{\theta},\underline{s})$ is nonzero at almost any $t$, even though $k(t,\underline{\theta},\underline{s})$ is zero-outside region $t \in (t_{min}, t_{max})$.

Note that the geometrical meaning of $t$ is retained through the Hilbert transform since the operation of equation (3) is shift-invariant. From this observation, the Hilbert transform of $f$ at location $\underline{x}$ on the line $L(\underline{\theta},\underline{s})$ has a clear meaning, namely that of $K(t,\underline{\theta},\underline{s})|t=(\underline{x}-\underline{s})\cdot\theta$. Furthermore, since $\underline{x}$ is on $L(\underline{\theta},\underline{s})$, this expression is independent of $\underline{s}$ and will be denoted as $$K*(\underline{\theta}, \underline{x}) = K(t, \underline{\theta}, \underline{s}) | t = (\underline{x} - \underline{s}) \cdot \theta \quad (4)$$
$$= K(t, \underline{\theta}, \underline{s}) | t = 0.$$

From equations (1)–(4), $$K*(\underline{\theta}, \underline{x}) = -\int_{-\infty}^{\infty} \frac{1}{\pi t} f(\underline{x} + t\underline{\theta}) dt \quad (5)$$

Also, note from this equation (5) that $K*(\underline{\theta},\underline{x})$ is odd in $\underline{\theta}$, i.e., $K*(-\underline{\theta},\underline{x}) = -K*(\underline{\theta},\underline{x})$.

The important parts of the above derivation are relations converting CB projections into values of $K*(\underline{\theta},\underline{x})$. If these values can be computed for points $\underline{x}$ that lie on the same line $L(\underline{\theta},\underline{s})$, a sampling of $K(t,\underline{\theta},\underline{s})$ is obtained as $$K*(\underline{\theta},\underline{x})|\underline{x}=\underline{s}=t\underline{\theta}=K(t,\underline{\theta},\underline{s}) \quad (6)$$

and if that sampling covers the whole region $[t_{min}, t_{max}]$, reconstruction of $f$ on $L(\underline{\theta},\underline{s})$ is possible as explained below.

It is well-known that the Hilbert transformation of $K(t,\underline{\theta},\underline{s})$ yields the negative of $k(t,\underline{\theta},\underline{s})$, i.e., $$k(t, \underline{\theta}, \underline{s}) = -\int_{-\infty}^{\infty} \frac{1}{\pi(t-t')} K(t', \underline{\theta}, \underline{s}) dt' \quad (7)$$

but this inversion result disregards knowledge on the support of $k(t,\underline{\theta},\underline{s})$ and consequently requires $K(t,\underline{\theta},\underline{s})$ to be known for all $t$. Since $k(t,\underline{\theta},\underline{s})$ is continuous in $t$ and zero outside $(t_{min}, t_{max})$, there exists a much less demanding inversion formula from the literature on integral equations. This equation (7) can be written as follows:

$$k(t, \underline{\theta}, \underline{s}) = \frac{C(\underline{\theta}, \underline{s}) - k_1(t, \underline{\theta}, \underline{s})}{w(t, \underline{\theta}, \underline{s})} \text{ for } t \in (t_{min}, t_{max}) \quad (8)$$

where $C(\underline{\theta},\underline{s})$ is a constant at fixed $(\underline{\theta},\underline{s})$, $$w(t, \underline{\theta}, \underline{s}) = \sqrt{(t - t_{min})(t_{max} - t)} \quad (9)$$

and $$k_1(t, \underline{\theta}, \underline{s}) = \int_{t_{min}}^{t_{max}} \frac{w(t', \underline{\theta}, \underline{s})}{\pi(t-t')} K(t', \underline{\theta}, \underline{s}) dt'. \quad (10)$$

Equation (8) shows that the portion of $K(t,\underline{\theta},\underline{s})$ defined with $t \in (t_{min}, t_{max})$ allows the recovery of $k(t,\underline{\theta},\underline{s})$ over its whole support up to a constant $C(\underline{\theta},\underline{s})$. This recovery essentially involves taking a simple Hilbert transform of a weighted version of $K(t,\underline{\theta},\underline{s})$ over the region $t \in (t_{min}, t_{max})$. It is, therefore, as efficient as equation (7), while less demanding on $K(t,\underline{\theta},\underline{s})$. Also, in the limit where $t_{min}$ and $t_{max}$ tend toward $-\infty$ and $+\infty$, respectively, equation (8) converges to equation (7) for a bounded $C(\underline{\theta},\underline{s})$, since $w(t',\underline{\theta},\underline{s})/w(t,\underline{\theta},\underline{s})$ converges toward 1. Equation (8) is a generalized version of equation (7).

The presence of the unknown, $C(\underline{\theta},\underline{s})$ in equation (8) shows, however, that $k(t,\underline{\theta},\underline{s})$ is not uniquely determined by the values of $K(t,\underline{\theta},\underline{s})$ over the region $t \in (t_{min}, t_{max})$. Additional information is needed to find $C(\underline{\theta},\underline{s})$. One approach is to use the sum of $f$ on the line $L(\underline{\theta},\underline{s})$. That is, if $$gL(\underline{\theta}, \underline{s}) = \int_{t_{min}}^{t_{max}} k(t, \underline{\theta}, \underline{s}) dt \quad (11)$$

is known, then from equation (8)

$$C(\underline{\theta}, \underline{s}) = \frac{gL(\underline{\theta}, \underline{s}) + \int_{t_{min}}^{t_{max}} \frac{k_1(t, \underline{\theta}, \underline{s})}{w(t, \underline{\theta}, \underline{s})} dt}{\int_{t_{min}}^{t_{max}} \frac{1}{w(t, \underline{\theta}, \underline{s})} dt}. \quad (12)$$

Alternatively, the vanishing of $k(t,\underline{\theta},\underline{s})$ at $t=t_{min}$ and $t=t_{max}$ can be used to get $$C(\underline{\theta},\underline{s}) = k_1(t_{min}, \underline{\theta}, \underline{s}) = k_1(t_{max}, \underline{\theta}, \underline{s}) \quad (13)$$

Both approaches are mathematically valid but present some challenges for numerical implementation. On one hand, equation (12) involves (integrable) singularities at $t=t_{min}$ and $t=t_{max}$ that require some careful numerical processing. On the other hand, equation (13) requires a very accurate knowledge of $k_1(t,\underline{\theta},\underline{s})$ at $t=t_{min}$ or $t=t_{max}$, which is not likely to be available in practice, due to discretization errors and data noise propagation.

Let $\epsilon$ be a small positive number and let $t_{min}^{\epsilon} = t_{min} - \epsilon$ and $t_{max}^{\epsilon} = t_{max} + \epsilon$. To overcome numerical problems, we substitute $t_{min}^{\epsilon}$ for $t_{min}$ and $t_{max}^{\epsilon}$ for $t_{max}$ in the right hand side of both equations (9) and (10) to obtain new quantities called $w_{\epsilon}(t,\underline{\theta},\underline{s})$ and $k_1^{\epsilon}(t,\underline{\theta},\underline{s})$. This substitution requires $K(t,\underline{\theta},\underline{s})$ to be known over a slightly larger domain but simplifies the numerical implementation because equation (8) may be replaced by $$k(t, \underline{\theta}, \underline{s}) = \chi_\varepsilon(t) \frac{C_\varepsilon(\underline{\theta}, \underline{s}) - k_1^\varepsilon(t, \underline{\theta}, \underline{s})}{w_\varepsilon(t, \underline{\theta}, \underline{s})} \text{ for } t \in [t_{min}^\varepsilon, t_{max}^\varepsilon] \qquad (14)$$

where $C_\varepsilon(\underline{\theta},\underline{s})$ is a new constant to be determined and where $\chi_\varepsilon(t)$ is any function that tends to zero when t tends to $t_{min}^\varepsilon$ and $t_{max}^\varepsilon$ and is equal to one in the region $[t_{min},t_{max}]$ where $k(t,\underline{\theta},\underline{s})$ may be nonzero. For example $$\chi_\varepsilon(t) = \begin{cases} 1, & \text{if } \tau(t) < d \\ \cos^2\left(\frac{\pi(d - \tau(t))}{2\varepsilon}\right), & \text{if } d < \tau(t) < d + \varepsilon, \\ 0, & \text{if } \tau(t) > d + \varepsilon \end{cases} \qquad (15)$$

with $d=(t_{min},t_{max})/2$ and $\sigma(t)=|t-(t_{min}+t_{max})/2|$. Repeating the process that led to equation (12) using equation (14) instead of equation (8) as a starting point, we get $$C_\varepsilon(\underline{\theta}, \underline{s}) = \frac{g_L(\underline{\theta}, \underline{s}) + \int_{t_{min}^\varepsilon}^{t_{max}^\varepsilon} \frac{\chi_\varepsilon(t) k_1^\varepsilon(t, \underline{\theta}, \underline{s})}{w_\varepsilon(t, \underline{\theta}, \underline{s})} dt}{\int_{t_{min}^\varepsilon}^{t_{max}^\varepsilon} \frac{\chi_\varepsilon(t)}{w_\varepsilon(t, \underline{\theta}, \underline{s})} dt} \qquad (16)$$

which does not include any singularity. Or following the ideas that led to equation (13), we get $$C_\varepsilon(\underline{\theta}, \underline{s}) = \frac{1}{2\varepsilon} \left[ \int_{t_{min}^\varepsilon}^{t_{min}} + \int_{t_{max}}^{t_{max}^\varepsilon} \right] k_1^\varepsilon(t, \underline{\theta}, \underline{s}) dt. \qquad (17)$$

Note that $\chi_\varepsilon(t)$ does not need to be smooth and could in particular be chosen as 1 for $\tau(t)<d$ and 0 otherwise, however, for the numerical implementation it is easier to use a smooth $\chi_\varepsilon(t)$ like that of equation (15).

The two approaches, equations (16) and (17), have been tested by the inventors and as disclosed in a separate paper on two-dimensional (2-D) classical tomography, see, F. Noo, R. Clackdoyle and J. D. Pack, "A Two-Step Hilbert Transform Method for 2D Image Reconstruction," *Phys. Med. Biol.*, Vol. 49, pp. 3903-23, 2004. Both approaches appear to perform equally well when ε is large enough to include a statistically representative set of samples of $k_1^\varepsilon(t,\underline{\theta},\underline{s})$ over the regions $t_{min}^\varepsilon<t<t_{min}$ and $t_{max}<t<t_{max}^\varepsilon$. Otherwise, equation (16) is more robust than equation (17). All the simulations disclosed below employ equation (16).

The following discussion defines the CB projections from which the reconstruction of $f$ is to be achieved, then introduces the concept of a differentiated backprojection (DBP) and shows how this concept links the CB projections to the Hilbert transform of $f$ on measured lines.

Let $\Omega^+$ be a bounded and convex neighborhood of $\Omega$. The results disclosed herein apply to CB projections measured on a source trajectory that consists of a union of $N \geq 1$ smooth curves $\Gamma_l, l=1,\ldots,N$ such that a neighborhood of each curve lies outside $\Omega^+$. To simplify the notation, this trajectory is described using a single parameter λ. The source position at λ is $\underline{a}(\lambda)$ and the domain of λ is a union of N disjoint intervals $\Lambda_l, l=1,\ldots,N$ each of which corresponds to one of the curves $\Gamma_l$ composing the trajectory, see, e.g., FIG. 2.

Figure 2:
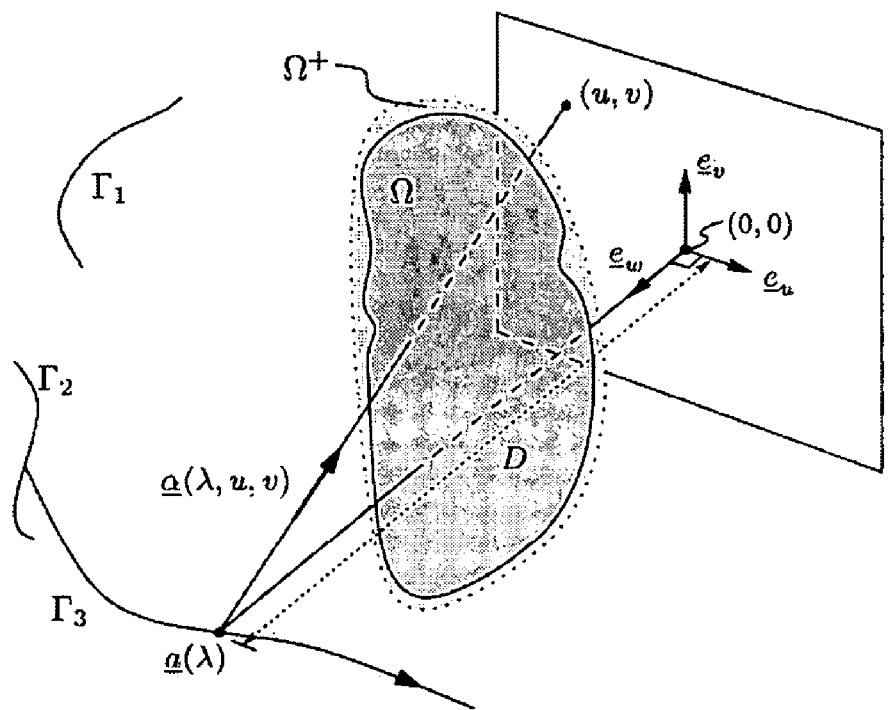
FIG. 2. is a diagram illustrating the data acquisition with a source trajectory consisting of 3 smooth curves ($\Gamma_1$, $\Gamma_2$, and $\Gamma_3$) according to an embodiment of the present invention.

FIG. 2. is a diagram illustrating the data acquisition with a source trajectory consisting of 3 smooth curves ($\Gamma_1, \Gamma_2$, and $\Gamma_3$). The source trajectory is described using a single parameter, $\Gamma_l$ and the source position at $\Gamma_l$ is $\underline{a}(\lambda)$. Also, the volume where $f$ is nonzero is $\Omega$, and there is a bounded and convex neighborhood, $\Omega^+$, of $\Omega$, such that a neighborhood of each source trajectory curve lies outside $\Omega^+$. Each CB projection can be fully described using a flat detector that intercepts all lines passing through the object. The detector plane is orthogonal to the unit vector, $\underline{e}_w$. The detector elements have coordinates u and υ along unit orthogonal vectors, $\underline{e}_u$ and $\underline{e}_\upsilon$, with $(u, \upsilon)=(0, 0)$ at the orthogonal projection of $\underline{a}(\lambda)$ onto the detector plane.

The smoothness of $\Gamma_l$ is related to the behavior of the tangent vector $\underline{a}'(\lambda)=d\underline{a}(\lambda)/d(\lambda)$ i.e., it is assumed that $\underline{a}'(\lambda)$ is bounded, continuous and nonzero over the interior of $\Lambda_l$ for any l. The nonvanishing condition on $\underline{a}'(\lambda)$ prohibits corners (angular points) on the $\Gamma_l$ curves. However, the source trajectory itself can have corners, for example a zigzag trajectory is admissible as it can be built by connections of line segments which are each smooth curves. Geometrically, the curves $\Gamma_l$ may overlap, intersect each other, or be simply connected.

One simple example trajectory is the circle-plus-line trajectory (see, e.g., F. Noo, R. Clackdoyle, and M. Defrise, "Direct Reconstruction of Cone-Beam Data Acquired with a Vertex Path Containing a Circle," *IEEE Trans, Image Process.*, Vol. 7, No. 6, pp. 854-67, Jun. 1998,) which consists of a circle and a line orthogonal to the plane of the circle. This trajectory may be described using N=2, $\Lambda_1=[0, 2\pi)$ and $\Lambda_2=[2\pi, 4\pi]$, with $$\underline{a}(\lambda) = \begin{cases} R_1\cos\lambda, R_1\sin\lambda, 0), & \text{if } \lambda \in \Lambda_1 \\ R_2, 0, (\lambda - 3\pi)\frac{H}{\pi}, & \text{if } \lambda \in \Lambda_2 \end{cases} \qquad (18)$$

where $R_1$, $R_2$, and H are free parameters (except for the condition that the source trajectory must be outside $\Omega^+$).

The CB projection at position λ is the set of integrals $$g(\lambda, \underline{\alpha}) \int_0^\infty f(\underline{a}(\lambda) + t\underline{\alpha}) dt \qquad (19)$$

obtained for all possible unit vectors $\underline{\alpha}$. However, since $\underline{\alpha}(\lambda)$ is outside $\Omega^+$ and $\Omega^+$ is convex, there exists a half sphere of unit vectors $\underline{\alpha}$ that do not point toward the object and for which g is consequently zero. Therefore, the CB projection can be fully described using a flat area detector placed on the opposite side of the object relative to the source, in a plane that intercepts all lines that diverge from the source and go through the object.

When using a flat area detector, the CB projection is denoted $g_A(\lambda,u,\upsilon)$, where u and υ are Cartesian coordinates in the detector plane. For convenience, the orthogonal projection of the source onto that plane is chose as the origin (u, υ)=(0, 0). This choice gives $$g_d(\lambda, u, v) = g(\lambda, \underline{\alpha}(\lambda, u, v)) \quad (20)$$

with $$\underline{\alpha}(\lambda, u, v) = \frac{1}{\sqrt{u^2 + v^2 + D^2}}(u\underline{e}_u + v\underline{e}_v - D\underline{e}_w) \quad (21)$$

where $\underline{e}_w$ is the unit vector orthogonal to the detector plane and pointing toward the source, $\underline{e}_u$ and $\underline{e}_v$ are orthogonal unit vectors in the direction along which u and v are measured, respectively, and D is the distance from the source to the detector plane (see FIG. 2). In general, $\underline{e}_u, \underline{e}_v, \underline{e}_w$ and D depend on $\lambda$, although this dependence is not written explicitly.

There exists an infinite number of possible orientations for a flat detector. When this orientation is such that $\underline{e}_u$ and $\underline{e}_w$ are, respectively, parallel and orthogonal to $\underline{a}'(\lambda)$, we say that the detector is well-oriented. Note that the requirement that the detector intercepts all lines diverging from the source toward the object is incompatible with having the detector well-oriented when the line of direction $\underline{a}'(\lambda)$ through $\underline{a}(\lambda)$ intersects the object. Hereafter, a reference to a well-oriented detector will always assume tacitly that the line of direction $\underline{a}'(\lambda)$ through $\underline{a}(\lambda)$ does not intersect $\Omega^+$, which is more that what is needed to avoid ambiguities but is convenient to simplify the developments.

By definition, the CB projection is truncated for a given source position $\underline{a}(\lambda)$ whenever there are values of u and v for which $g_d(\lambda, u, v)$ is known (measured) on all lines that diverge from $\underline{a}(\lambda)$ and pass through a neighborhood of that set.

The inventive method that allows conversion of CB projections into Hilbert transforms of $f$ on measured lines is a version of a filtered-backprojection procedure, referred to herein as the differentiated backprojection (DBP). This method may be applied to any segment of the smooth curves forming the source trajectory. The method may be best understood as a 3-D extension of the 2-D DBP introduced in F. Noo, R. Clackdoyle and J. D. Pack, "A Two-Step Hilbert Transform Method for 2D Image Reconstruction," *Phys. Med. Biol.*, Vol. 49, pp. 3903-23, 2004. For a well-oriented detector, a DBP appears equivalent to the application of the filtered backprojection steps of Feldkamp et al., upon removal of the Hilbert kernel from the ramp filter. This essentially corresponds to replacing the ramp filter of Feldkamp et al., by a differentiation filter. More specifically, a DBP for a well-oriented detector is achieved using the following three method steps. See FIGS. 2 and 3 for an illustration of some of the involved quantities.

Step 1) Weight each projection to obtain $$\overline{g}(\lambda, u, v) = \frac{D}{\sqrt{u^2 + v^2 + D^2}} g_d(\lambda, u, v) \quad (22)$$

Step 2) Differentiate each weighted projection in u to obtain $$g_F(\lambda, u, v) = \frac{\partial}{\partial u} \overline{g}(\lambda, u, v). \quad (23)$$

Step 3) Apply the weighted CB backprojection step of Feldkamp et al. to $g_F$ over any segment $[\lambda_1, \lambda_2]$ of one of the smooth curves $\Gamma_l$ forming the source trajectory to obtain $$b(\underline{x}, \lambda_1, \lambda_2) = \int_{\lambda_1}^{\lambda_2} \frac{D \|\underline{a}'(\lambda)\| g_F(\lambda, u^*(\lambda, \underline{x}), v^*(\lambda, \underline{x}))}{[(\underline{a}(\lambda) - \underline{x}) \cdot \underline{e}_w]^2} d\lambda \quad (24)$$

at any $\underline{x} \in \Omega^+$, where $u^*(\lambda, \underline{x})$ and $v^*(\lambda, \underline{x})$ are the detector coordinates of the line that connects $\underline{x}$ to $\underline{a}(\lambda)$, i.e., $$u^*(\lambda, \underline{x}) = -D \frac{(\underline{x} - \underline{a}(\lambda)) \cdot \underline{e}_u}{(\underline{x} - \underline{a}(\lambda)) \cdot \underline{e}_w} \quad (25)$$

$$v^*(\lambda, \underline{x}) = -D \frac{(\underline{x} - \underline{a}(\lambda)) \cdot \underline{e}_v}{(\underline{x} - \underline{a}(\lambda)) \cdot \underline{e}_w} \quad (26)$$

Figure 3:
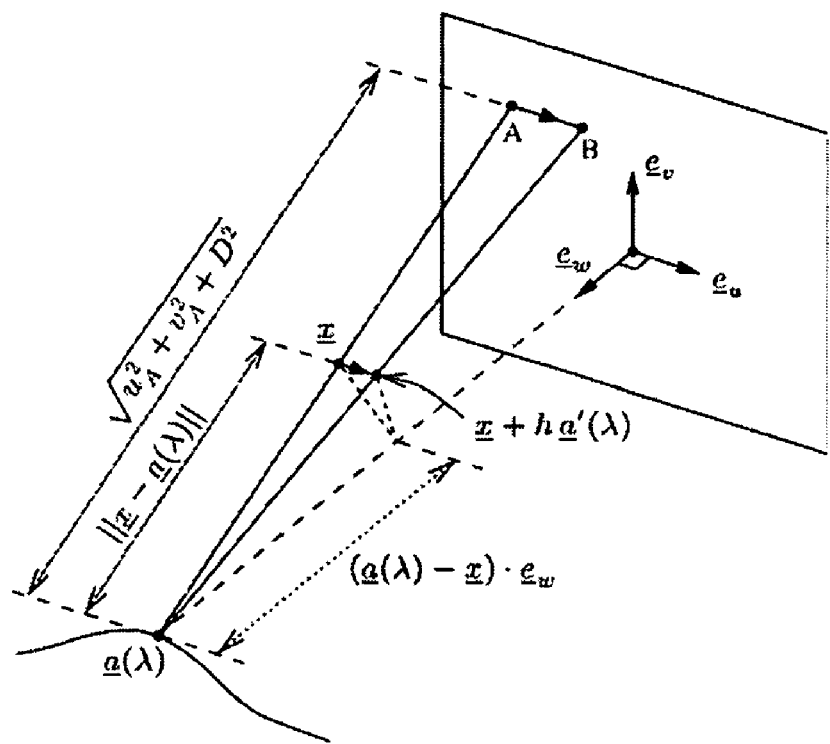
FIG. 3 is a diagram illustrating projection geometry for a well-oriented detector according to an embodiment of the present invention.

FIG. 3 is a diagram illustrating projection geometry for a well-oriented detector according to an embodiment of the present invention. Point A is the projection of $\underline{x}$ and has, thus, coordinates $u_A = u^*(\lambda, \underline{x})$ and $v_A = v^*(\lambda, \underline{x})$ given by equations (25) and (26). When translating $\underline{x}$ in the direction of $\underline{a}'(\lambda)$ by h: (1) the projection of $\underline{x}$ moves from A to B in the direction of $\underline{e}_u$, yielding $v_B = v_A$ for the $v$-coordinate of B and (2) the projected distance between $\underline{a}(\lambda)$ and $\underline{x}$ along the axis $\underline{e}_w$ remains constant.

By definition, the outcome b of a DBP depends on the $\lambda$-interval over which the backprojection is carried out. This dependence is written down explicitly in the arguments of b, using the values $\lambda_1$ and $\lambda_2$ that define the endpoints of the backprojection range. Furthermore, as stated above in equation (24), there exists a value of l such that $[\lambda_1, \lambda_2] \subset \Lambda_l$; the DBP is always defined over one smooth segment of the source trajectory.

The DBP concept is a CB generalization of a method that yields the Hilbert transform of $f$ from fan-beam projections in 2-D. However, since there may exist several ways to have a detector well-oriented, it seems natural to ask whether the DBP is really a well-defined (detector-independent) concept. The rest of this section of the detailed description proves this assertion and also explains how to extend the definition of the DBP to a flat detector that is not well-oriented.

To understand why the DBP of the present invention is independent of the way the detector is well-oriented, a more general expression needs to be adopted for b, namely $$b(\underline{x}, \lambda_1, \lambda_2) = \int_{\lambda_1}^{\lambda_2} \left[ \frac{d}{dh} g_e(\lambda, \underline{x} + h\underline{a}'(\lambda) - \underline{a}(\lambda)) \right]_{h=0} d\lambda \quad (27)$$

where $g_e$ is the homogeneous extension of degree-1 of the CB projection g in $\underline{\alpha}$, i.e., $$g_e(\lambda, \underline{z}) = \frac{1}{\|\underline{z}\|} g\left(\lambda, \frac{\underline{z}}{\|\underline{z}\|}\right) \text{ for any } \underline{z} \neq 0 \quad (28)$$

or, from equations (19) and (28)

$$g_e(\lambda, \underline{z}) = \int_0^\infty f(\underline{a}(\lambda) + t\underline{z}) dt \text{ for any } \underline{z} \neq 0. \quad (29)$$

Equation (27) is clearly detector-independent and, like equation (24), defines the DBP as a description of how a backprojection at a given $\underline{x}$ varies when $\underline{x}$ is slightly moved in the direction of $\underline{a}'(\lambda)$ during the backprojection.

To prove that equation (27) is equivalent to equation (24) for a well-oriented detector, note first from equation (28) that $$g_e(\lambda, \underline{x} - \underline{a}(\lambda)) = \frac{g_d(\lambda, u^*(\lambda, \underline{x}), v^*(\lambda, \underline{x})}{\|\underline{x} - \underline{a}(\lambda)\|} \quad (30)$$

$$= \frac{\overline{g}(\lambda, u^*(\lambda, \underline{x}), v^*(\lambda, \underline{x})}{(\underline{a}(\lambda) - \underline{x}) \cdot \underline{e}_w}$$

where $u^*(\lambda,\underline{x})$ and $v^*(\lambda,\underline{x})$ are the quantities of equations (25) and (26), and where $\overline{g}$ is the weighted projection of equation (22), see FIG. 3. The substitution of $\underline{x}+h\underline{a}'(\lambda)$ for $\underline{x}$ in equation (30) gives access to a detector-coordinate expression of the integrand in equation (27). In the particular case of a well-oriented detector, both the denominator in equation (30) and the expression of $\epsilon^*$ are unaffected by this substitution because $\underline{a}'(\lambda)$ is parallel to $\underline{e}_u$ and orthogonal to $\underline{e}_w$. So, the dependence in h of the value of $g_e$ in equation (27) comes only from a difference in values of $u^*$, i.e., $$g_e(\lambda, \underline{x} + h\underline{a}'(\lambda) - \underline{a}(\lambda)) = \frac{\overline{g}(\lambda, u^*(\lambda, \underline{x} + h\underline{a}'(\lambda)), v^*(\lambda, \underline{x})}{(\underline{a}(\lambda) - x) \cdot \underline{e}_w} \quad (31)$$

see again FIG. 3. The differentiation of this expression with respect to h followed by a setting of h to zero directly yields equation (24) from equation (27) because from equation (25)

$$u^*(\lambda, \underline{x} + h\underline{a}'(\lambda)) = u^*(\lambda, \underline{x}) + h\frac{D\|\underline{a}'(\lambda)\|}{(\underline{a}(\lambda) - x) \cdot \underline{e}_w} \quad (32)$$

for any well-oriented detector.

For a detector that is not well-oriented, the DBP is obtained from the substitution of $\underline{x}+h\underline{a}'(\lambda)$ for $\underline{x}$ in equation (30) that yields a detector-coordinate expression of equation (27). Straightforward but lengthy calculations show that the DBP for an arbitrarily oriented detector remains that of equation (24) provided the following expression for $g_F$ is used instead of equation (23)

$$g_F(\lambda, u, v) = \underline{e}_T \cdot \left(\underline{e}_u + \frac{u\underline{e}_w}{D}\right)\frac{\partial \overline{g}}{\partial u} + \quad (33)$$

$$\underline{e}_T \cdot \left(\underline{e}_v + \frac{v\underline{e}_w}{D}\right)\frac{\partial \overline{g}}{\partial v} - \underline{e}_T \cdot \underline{e}_w \frac{\overline{g}}{D}$$

where $\underline{e}_T$ is the unit vector along $\underline{a}'(\lambda)$, i.e., $\underline{e}_T = \underline{a}'(\lambda)/\|\underline{a}'(\lambda)\|$.

Figure 4:
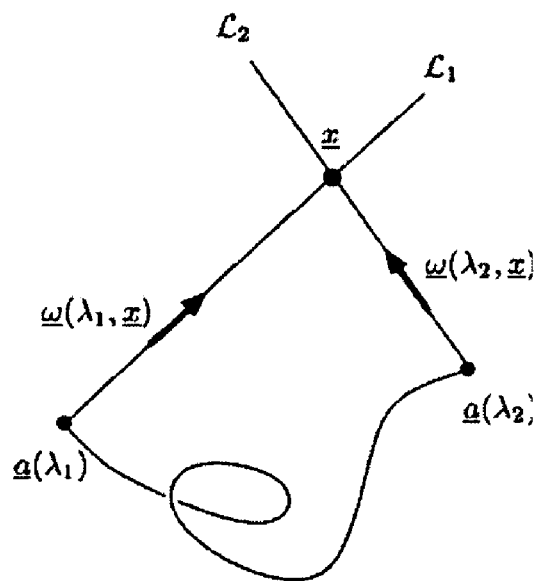
FIG. 4 is an illustration of the link between the DBP and the Hilbert transform according to an embodiment of the present invention.

FIG. 4. is an illustration of the link (equation (34)) between the DBP and the Hilbert transform. For $\underline{x} \in \Omega$, the DBP over $[\lambda_1, \lambda_2]$ with the addition of boundary terms yields the difference between two Hilbert transforms of $f$ at $\underline{x}$, namely that on the line $L_2$ in the direction of $\underline{\omega}(\lambda_2,\underline{x})$, and that on the line $L_1$ in the direction of $\underline{\omega}(\lambda_2,\underline{x})$.

As stated above, the DBP provides a link between CB projections and the Hilbert transform of $f$ on measured lines. Using the equations (1)-(6), this link can be written in the following form: for any $\underline{x} \in \Omega^+$, $$1/\pi b_a(\underline{x},\lambda_1,\lambda_2) = K^*(\underline{\omega}(\lambda_2,\underline{x}),\underline{x}) - K^*(\underline{\omega}(\lambda_1,\underline{x}),\underline{x}) \quad (34)$$

where $$\underline{\omega}(\lambda, \underline{x}) = \frac{\underline{x} - \underline{a}(\lambda)}{\|\underline{x} - \underline{a}(\lambda)\|} \quad (35)$$

and where $$b_a(\underline{x}, \lambda_1, \lambda_2) = b(\underline{x}, \lambda_1, \lambda_2) + \sum_{q=1}^{2} \frac{(-1)^q g(\lambda_q, \underline{\omega}(\lambda_q, \underline{x}))}{\|\underline{x} - \underline{a}(\lambda_q)\|} \quad (36)$$

is the DBP at $\underline{x}$ over the interval $[\lambda_1, \lambda_2]$ with added boundary terms.

For a geometric interpretation of equation (34), picture the two lines $L_1$ and $L_2$ that connect $\underline{a}(\lambda_1)$ and $\underline{a}(\lambda_2)$ to $\underline{x}$, respectively, as shown in FIG. 4. Then, picture the Hilbert transform of $f$ at $\underline{x}$ on both lines, $L_1$ and $L_2$, in the direction from $\underline{a}(\lambda_1)$ to $\underline{x}$ and from $\underline{a}(\lambda_2)$ to $\underline{x}$, respectively. These two directions are those given by $\underline{\omega}(\lambda_1,\underline{x})$ and $\underline{\omega}(\lambda_2,\underline{x})$. The Formula in equation (34) states that the difference between these two Hilbert transforms at $\underline{x}$ is proportional to $b_a(\underline{x},\lambda_1,\lambda_2)$, where $b_a(\underline{x},\lambda_1,\lambda_2)$ is obtained by adding two boundary terms to the DBP over the segment of source trajectory joining $\underline{a}(\lambda_1)$ to $\underline{a}(\lambda_2)$. Note that the two boundary terms added to the DBP are just the ratios of the CB measurements on $L_1$ and $L_2$ to the distances from $\underline{x}$ to $\underline{a}(\lambda_1)$ and $\underline{a}(\lambda_2)$, respectively.

In general, the usefulness of equation (34) for CB reconstruction is not at all obvious since equation (34) only gives access to differences between Hilbert-transform values. However, when there exists an R-line through $\underline{x}$, the situation becomes wholly different, and equation (34) is found to deliver two fundamental formulas for CB reconstruction. These two formulas can be stated as follows:

Formula F1: If $\underline{a}(\lambda_1)$ and $\underline{a}(\lambda_2)$ are two arbitrary positions on one of the smooth curves forming the source trajectory, then $$K^*(\underline{\omega}(\lambda_1, \underline{x}),\underline{x}) = \frac{-1}{2\pi} b_a(\underline{x}, \lambda_1, \lambda_2) \quad (37)$$

for any $\underline{x} \in \Omega^+$ that is on the line joining $\underline{a}(\lambda_1)$ to $\underline{a}(\lambda_2)$.

Formula F2: If $\underline{a}(\lambda_1)$, $\underline{a}(\lambda_2)$ and $\underline{a}(\lambda_3)$ are three arbitrary positions on one of the smooth curves forming the source trajectory, then $$K^*(\underline{\omega}(\lambda_3, \underline{x}),\underline{x}) = \frac{-1}{2\pi}(b_a(\underline{x}, \lambda_3, \lambda_1) + b_a(\underline{x}, \lambda_3, \lambda_2)) \quad (38)$$

for any $\underline{x} \in \Omega^+$ that is on the line joining $\underline{a}(\lambda_1)$ to $\underline{a}(\lambda_2)$.

Formulas F1 and F2 each give a way to obtain samples of the Hilbert transform of $f$ on measured lines, and provide thereby a basis for CB reconstruction as discussed previously and expanded in the next section. Note, however, that formula F1 is more restrictive than formula F2 as it yields only samples of the Hilbert transform of $f$ on R-lines. In fact, formula F1 is just the particular case of formula F2 defined with $\lambda_3=\lambda_1$, but formula F1 is sufficiently useful to be individually stated.

To obtain formula F1, as previously stated recall that $K^*$ is odd in its first argument, and note that $\underline{\omega}(\lambda_2,\underline{x})=-\underline{\omega}(\lambda_1,\underline{x})$ for $\underline{x}$ on the R-line from $\underline{a}(\lambda_1)$ to $\underline{a}(\lambda_2)$, Hence, under the conditions of formula F1, the right hand side of equation (34) is $-2K^*(\underline{\omega}(\lambda_1,\underline{x}),\underline{x})$, and equation (34) is equivalent to equation (37).

Formula F2 is obtained by applying equation (34) twice to get $$1/\pi b_a(\underline{x},\lambda_3,\lambda_1)=K^*(\underline{\omega}(\lambda_1,\underline{x}),\underline{x})-K^*(\underline{\omega}(\lambda_3,\underline{x}),\underline{x}) \quad (39)$$

$$1/\pi b_a(\underline{x},\lambda_3,\lambda_2)=K^*(\underline{\omega}(\lambda_2,\underline{x}),\underline{x})-K^*(\underline{\omega}(\lambda_3,\underline{x}),\underline{x}). \quad (40)$$

Since $K^*(\underline{\omega}(\lambda_2,\underline{x}),\underline{x})=-K^*(\underline{\omega}(\lambda_1,\underline{x}),\underline{x})$ under the conditions of formula F2, the addition of these two equations side to side immediately yields formula F2.

A proof of equation (34) is now given. Consider the general expression of equation (27) for the DBP using the notation $G_e(\lambda,\underline{x})$ for the integrand in that expression. For $\underline{x}\in\Omega^+$, equation (29) yields $$G_e(\lambda, \underline{x}) = \left[\frac{d}{dh}\int_0^\infty f(\underline{a}(\lambda) + t(\underline{x} + h\underline{a}'(\lambda) - \underline{a}(\lambda)))\,dt\right]_{h=0} \quad (41)$$

$$= \left[\frac{d}{dh}\int_{-\infty}^\infty f(\underline{a}(\lambda) + t(\underline{x} + h\underline{a}'(\lambda) - \underline{a}(\lambda)))\,dt\right]_{h=0}$$

because $\underline{a}(\lambda)$ is outside $\Omega^+$ while $\underline{x}+h\underline{a}'(\lambda)$ is in $\Omega^+$ for h small enough since $\Omega^+$ is open. We insert the derivative with respect to h inside the integral of equation (41) and use the chain rule to find $$G_e(\lambda, \underline{x}) = \int_{-\infty}^\infty t\underline{a}'(\lambda)\cdot(\vec{\nabla}f)(\underline{a}(\lambda) + t(\underline{x} - \underline{a}(\lambda)))\,dt. \quad (42)$$

Then, we apply again the chain rule to find $$\frac{d}{d\lambda}f(\underline{\xi}) = (1-t)\underline{a}'(\lambda)\cdot(\vec{\nabla}f)(\underline{\xi}) \quad (42)$$

for $\underline{\xi}=\underline{a}(\lambda)+t(\underline{x}-\underline{a}(\lambda))$ and, thus, from equation (42)

$$G_e(\lambda, \underline{x}) = \int_{-\infty}^\infty \frac{t}{1-t}\frac{d}{d\lambda}f(\underline{a}(\lambda) + t(\underline{x} - \underline{a}(\lambda)))\,dt \quad (44)$$

$$= \frac{d}{d\lambda}\int_{-\infty}^\infty \frac{t}{1-t}f(\underline{a}(\lambda) + t(\underline{x} - \underline{a}(\lambda)))\,dt$$

which yields from $t/(1-t)=-1+1/(1-t)$ and equation (29)

$$G_e(\lambda, \underline{x}) = \frac{d}{d\lambda} \quad (45)$$

$$\left\{-g_e\left(\lambda, \underline{x} - \underline{a}(\lambda)\right) + \int_{-\infty}^\infty \frac{t}{1-t}f(\underline{a}(\lambda) + t(\underline{x} - \underline{a}(\lambda)))\,dt\right\}.$$

Next, the following change of variable $$t = 1 + \frac{\tau}{\|\underline{x}-\underline{a}(\lambda)\|}, \quad \frac{dt}{1-t} = \frac{d\tau}{\tau} \quad (46)$$

is applied along with equations (5), (28), and (35) to get $$G_e(\lambda, \underline{x}) = \frac{d}{d\lambda}\left\{\frac{-g(\lambda, \omega(\lambda, \underline{x}))}{\|\underline{x}-\underline{a}(\lambda)\|} + \pi K^*(\underline{\omega}(\lambda, \underline{x}), \underline{x})\right\}. \quad (47)$$

Integrating $G_e(\lambda,\underline{x})$ in $\lambda$ according to the expression of the DBP in equation (27), of which $G_e(\lambda,\underline{x})$ is the integrand, yields directly equation (34) upon some rearrangement of the resulting terms. Note that the conditions assumed on $f$, $\Omega^+$, and the source trajectory justifies the manipulations hereabove, but may not all be necessary; minimum conditions yielding equation (34) were not investigated.

The following discussion investigates the impact of formulas F1 and F2 on reconstruction from CB projections on a source trajectory that consists of a single smooth curve. The impact of formula F1 is discussed first. Next, the added advantages of formula F2 are investigated. In each case, results from computer-simulated data are provided in support of the theory. As in the previous sections, the theory presented here applies to general source trajectories. However, the discussion and examples are mostly focused on a helical trajectory because a good knowledge about the properties of the source trajectory is required for a proficient application of our results. Such properties have only been documented for the helix and the less familiar saddle trajectories, see e.g., J. D. Pack, F. Noo and H. Kudo, "Investigation of Saddle Trajectories for Cardiac CT Imaging in Cone-Beam Geometry," *Phys. Med. Biol.*, Vol. 49, No. 11, pp. 2317-36.

Note that we are only interested in recovering $f$ at points inside $\Omega$. For this reason, $\Omega^+$ does not appear explicitly in the discussion and equations below. However, the fact that the DBP is defined over $\Omega^+$ is heavily used because the convex hull of the intersection of a line with $\Omega$ does not generally lie in $\Omega$ but in $\Omega^+$ and the DBP over that convex hull is needed for our developments.

The following is a discussion on reconstruction on R-lines. Recall from above that formula F1 provides a means to obtain samples of the Hilbert transform of $f$ on R-lines, and recall from Section II-B that $f$ can be recovered on any line L in space when the Hilbert transform of $f$ on L is known over the convex hull of the intersection of L with $\Omega$. Combining these two results together, a procedure is obtained for reconstruction of $f$ on any R-line that intersects $\Omega$. Let $\underline{a}(\lambda_1)$ and $\underline{a}(\lambda_2)$ be the endpoints of the R-line, and let $\underline{\theta}_{12}$ be the unit vector in the direction from $\underline{a}(\lambda_1)$ to $\underline{a}(\lambda_2)$. Following the notation of developed above, the expression for $f$ on the R-line and its Hilbert transform are given by the functions $k(t,\underline{\theta}_{12},\underline{a}(\lambda_1))$ and $K(t,\underline{\theta}_{12},\underline{a}(\lambda_1))$, respectively, see equations (2) and (3). Using this notation the reconstruction procedure according to an embodiment of the present invention may be described in the following three steps.

1) Determine the region $[t_{min},t_{max}]$ that defines the convex hull of the intersection of the R-line with $\Omega$.
2) Use formula F1 to get the Hilbert transform of $f$ on the R-line for $t\in(t_{min},t_{max})$, i.e., compute $$K(t, \underline{\theta}_{12}, \underline{a}(\lambda_1)) = -\frac{1}{2\pi} b_a(\underline{r}, (t, \underline{\theta}_{12}, \underline{a}(\lambda_1)), \lambda_1, \lambda_2 \quad (48)$$

from the CB projections for any t∈($t_{min}$,$t_{max}$) where $\underline{r}$,(t, $\underline{\theta}_{12}$,$\underline{a}(\lambda_1)$)) is the position vector on the R-line given by equation (1).

3) Apply equation (8) to obtain k(t,$\underline{\theta}_{12}$,$\underline{a}(\lambda_1)$) from K(t,$\underline{\theta}_{12}$, $\underline{a}(\lambda_1)$)) for any t∈($t_{min}$,$t_{max}$).

Note that equation (48) is simply a rewriting of equation (37) using $\underline{r}$,(t,$\underline{\theta}_{12}$,$\underline{a}(\lambda_1)$) for $\underline{x}$ following equation (6).

The above reconstruction procedure is similar to the method suggested by Zou and Pan for reconstruction on π-lines in HCBT (helical CB tomography) but is not limited to π-lines nor to a helical trajectory. Even so, it only applies to points on R-lines and is, therefore, too restrictive for some source trajectories since the set of points where Tuy's condition is satisfied is in general larger than the set of points that belong to R-lines. However, this drawback is offset by a low request on detector coverage. To achieve reconstruction on an R-line as described above, we just need to guarantee the DBP (with boundary terms) in equation (48) can be computed at all required t. Using the visibility concept described above, this requirement yields the following data completeness condition:

Accurate reconstruction on an R-line is possible whenever the convex hull of the intersection of the R-line with Ω is visible while the source travels between the endpoints of the R-line.

This condition requires little compared to what all previously published CB reconstruction methods would require for reconstruction at points on an R-line. A good illustration of this feature is obtained in the particular case of HCBT, where the CB projection of a π-line from a source position between its endpoints is just a line segment connecting a point on the lower boundary of the TD (Tam-Danielsson) detector window to a point on the upper boundary of this window. See FIG. 5 and discussion below which compares at various source positions between the endpoints of a central π-line the detector region required by the above procedure for reconstruction on that π-line. The difference is clearly significant. Looking at this difference from a global viewpoint, Zou and Pan stated that accurate reconstruction of the entire FOV with the same (low) overscan as Katsevich's formula is possible using only the data inside the TD window. In addition to this global viewpoint, we note from FIG. 5 that there are projections in which lateral parts of the FOV (and, thus, the imaged object) need not be irradiated for reconstruction on a π-line, i.e., transverse truncation is admissible at some source positions, unlike with Katsevich's formula.

FIG. 5 illustrates representations of a detector at three source positions between the endpoints of a central π-line L on a helix according to embodiments of the present invention. The light gray region is the projection of a central cylinder that encloses Ω. Reconstruction of f on the intersection of L with this cylinder using the R-line method disclosed herein requires data in the black region. This black region is much smaller than that needed to apply Katsevich's formula, i.e., the dark gray region.

The inventors have closely examined the R-line reconstruction procedure described herein in terms of transverse truncation in HCBT and have made the following observations. Consider a helical scan with a pitch small enough for the detector area to include the TD window, and consider a patient that extends outside the FOV in the x-direction (the direction orthogonal to sagittal slices) as illustrated in FIG. 6A. Given the projection geometry, the DBP is computable at any point in the FOV. Furthermore, the π-lines parallel to the (y,z)-plane through the FOV have their intersection with the patient almost always completely included in the FOV, as shown in FIG. 6A. Hence, accurate reconstruction is possible on the shaded surface on π-lines seen in that figure, even though the projections are transversely truncated on both sides at some source positions. Unfortunately, the situation is different for π-lines parallel to the (x, z)-plane through the FOV, as illustrated in FIG. 6B. The intersection of most of these π-lines with the patient extends outside the FOV, preventing a complete computation of the DBP on that intersection, and making it impossible to accurately reconstruct f anywhere on the π-line according to the method of the present invention as disclosed in this section. Combining positive and negative observations, we can state that despite the presence of transverse truncation in some projections, the R-line reconstruction procedure disclosed above allows accurate reconstruction over the volume defined by the π-lines whose intersection with the patient is fully included in the FOV. Depending on the amount of truncation, this volume may or may not be significant.

FIGS. 6A and 6B illustrate axial views of a single-turn helical scan of a patient that extends beyond the FOV (dashed circle) in the x-direction according to embodiments of the present invention. In FIG. 6A the data is complete for an R-line reconstruction (the method of Section IV-A) on most π-lines parallel to the (y, z)-plane through the FOV (see the large shaded area). In FIG. 6B the data is incomplete for an R-line reconstruction on most π-lines that are parallel to the (x, z)-plane.

Experiments from computer-simulated data of the FORBILD head phantom without the ears have been performed to test the accuracy of an embodiment of the R-line reconstruction method of the present invention described above. See Friedrich-Alexander-University Erlangen-Nürnberg, Institute of Medical Physics, Erlangen, Germany (online), available at: www.imp.uni-erlangen.de/forbild/english/results/index.htm for a description of the FORBILD head phantom. These experiments used the helical trajectory of $$\underline{a}(\lambda) = \left(R\cos\lambda, R\sin\lambda, \frac{P\lambda}{2\pi}\right) \quad (49)$$

and the saddle trajectory of $$\underline{a}(\lambda) = (R\cos\phi\cos\lambda, R\cos\phi\sin\lambda, R\sin\phi) \quad (50)$$

with $\phi = \arctan\left(\frac{P}{R}\cos 2\lambda\right)$ where in each case λ is the polar angle in the (x,y)-plane, and P and R are shaped parameters. Note that equation (5) was referred to as the X-saddle in J. D. Pack, F. Noo and H. Kudo, "Investigation of Saddle Trajectories for Cardiac CT Imaging in Cone-Beam Geometry," *Phys. Med. Biol.*, Vol. 49, No. 11, pp. 2317-36.

where in each case λ is the polar angle in the (x, z)-plane, and P and R are shaped parameters. Note that equation (5) was referred to as the X-saddle in J. D. Pack, F. Noo and H. Kudo, "Investigation of Saddle Trajectories for Cardiac CT Imaging in Cone-Beam Geometry," *Phys. Med. Biol.*, Vol. 49, No. 11, pp. 2317-36.

Figure 7A:
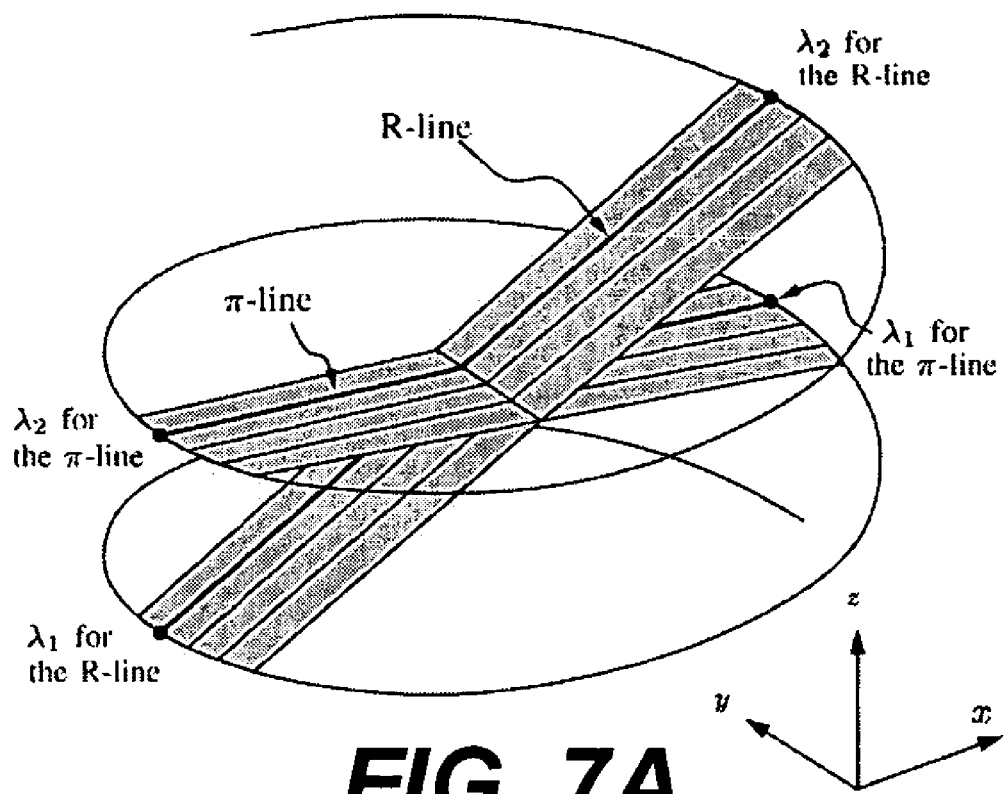
FIG. 7A is an exaggerated-pitch illustration of a surface of π-lines and a surface of R-lines (that are not π-lines) on which helical reconstructions were achieved according to an embodiment of the present invention.
Figure 7B:
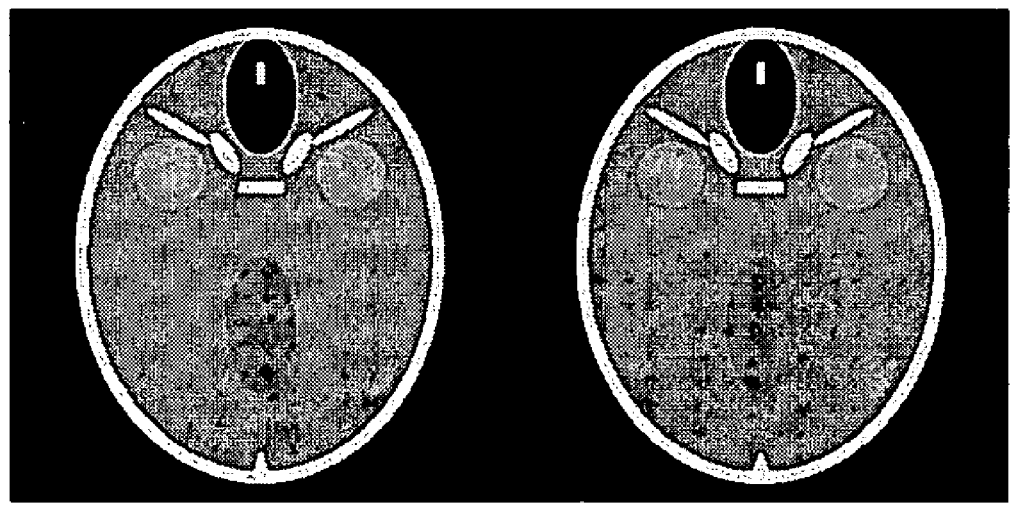
FIG. 7B illustrates true images of the FORBILD head phantom without ears on the π-line (left side) and the R-line (right side) surfaces according to an embodiment of the present invention.

Helical CB projections were simulated with and without Poisson noise corresponding to an emission of 300,000 photons per ray, using R=57 cm and P=3.24 cm. There were 1160 projections per turn, the detector plane was parallel to the z-axis at distance D=104 cm from the source, the u-axis was parallel to the (x, y)-plane, and the projections were discretized on a grid of square pixels of size 0.14 cm. Reconstructions were then achieved on two sets of R-lines parallel to the (x, y)-plane as illustrated in FIG. 7A. The R-lines in the first set were π-lines, while the R-lines in the second set were lines connecting vertices separated by a polar angle between $2\pi$ and $4\pi$. Each set of R-lines formed a surface that was parameterized in (x, y) for display and reconstruction purposes, using square pixels of side 0.075 cm. The structures of the phantom over the two surfaces of R-lines are shown in FIG. 7B. Note how the eyes appear to have different sizes as a consequence of the obliqueness of the R-lines relative to the (x, y)-plane. In an axial (z) slice, the eyes would have the same size.

FIG. 7A is an exaggerated-pitch illustration of a surface of π-lines and a surface of R-lines (that are not π-lines) on which helical reconstructions were achieved. FIG. 7B illustrates true images of the FORBILD head phantom without ears on the π-line (left side) and the R-line (right side) surfaces. The images are displayed with a compressed grayscale of 100 HU covering the values from 0 to 100 HU.

Figure 8:
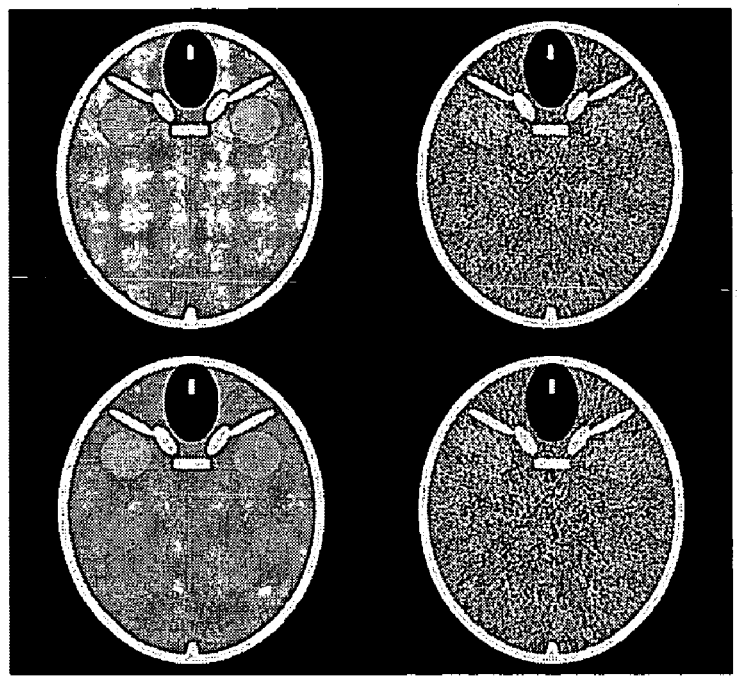
FIG. 8. illustrates reconstructions of the FORBILD head phantom without ears on the π-line surface of FIG. 7A, according to an embodiment of the present invention.

FIG. 8. illustrates reconstructions of the FORBILD head phantom without ears on the π-line surface of FIG. 7A. Reconstructions with (right side) and without (left side) noise added to the data are shown in FIG. 8. The top row in FIG. 8 illustrate results obtained using an embodiment of the method of the present invention. The bottom row in FIG. 8 illustrates results obtained using the prior art method of Katsevich. The grayscale in FIG. 8 is: 0 to 100 HU.

Figure 9:
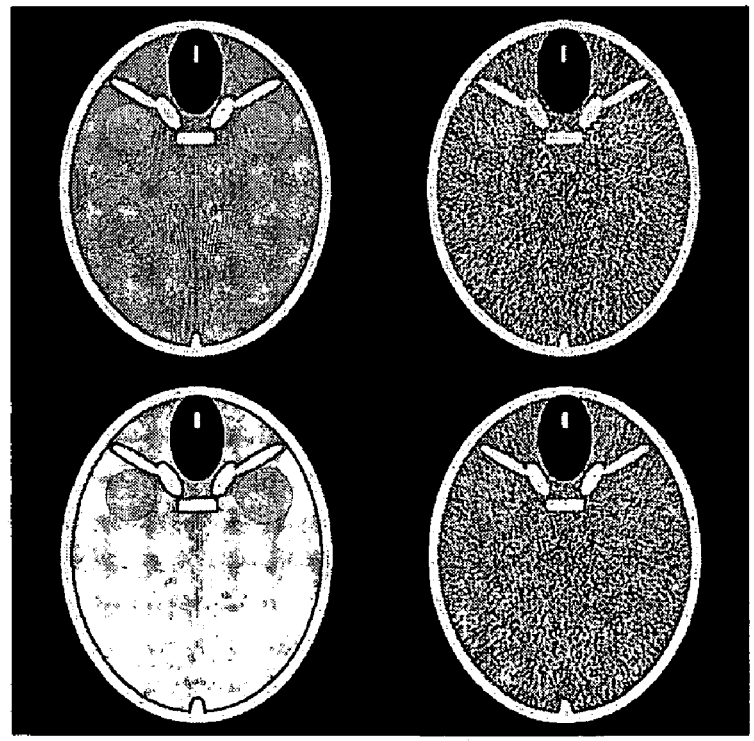
FIG. 9. illustrates reconstructions of the FORBILD head phantom without ears on the surface of R-lines (that are not π-lines) of FIG. 7A according to embodiments of the present invention.

FIG. 9 illustrates reconstructions of the FORBILD head phantom without ears on the surface of R-lines (that are not π-lines) of FIG. 7A. Reconstructions with (right side) and without (left side) noise added to the data are shown. The top row in FIG. 9 illustrates results obtained using embodiments of the method of the present invention. The bottom row in FIG. 9 illustrates results obtained by computing the output of Katsevich's formula onto the R-line surface. The grayscale in FIG. 9 is: 0 to 100 HU.

FIGS. 8 and 9 compare two reconstruction results for the first and the second surface of R-lines respectively, obtained using discretization techniques similar to those disclosed in F. Noo, J. Pack and D. Heuscher, "Exact Helical Reconstruction Using Native Cone-Beam Geometries," *Phys. Med. Biol.*, Vol. 48, pp. 3787-818. The result shown in FIG. 8 was computed using the formulas according to methods of the present invention. The result shown in FIG. 9 was obtained by computing the output of Katsevich's formula onto the points forming the surface of R-lines. In each case, the R-line reconstructions appeared in good agreement with the theory supporting them. Furthermore, the R-line method performed as well as Katsevich's formula on the surface of π-lines (FIG. 8), while using less data. For the other surface of R-lines (FIG. 9), the situation was different, i.e., the R-line reconstruction was noisier while requiring data in the 3π window that is about 3 times larger than the TD window. For a discussion on the 3π window, see R. Proksa, T. Köhler, M. Grass and J. Timmer, "The n-Pi-Method for Helical Cone-Beam CT," *IEEE Trans. Med. Imag.*, Vol. 19, No. 9, pp. 848-63, September 2000.

While counterintuitive, this increase in noise is not surprising when one considers what happens as R tends to ∞ while P remains fixed. In that limit, the R-lines become identical to the π-lines, and the intervals [π/2, 3π/2], [3π/2,5π/2] and [5π/2,7π/2] of source positions each provide enough information for computation of the Hilbert transform of $f$ on the R-lines. However, the sign of the Hilbert transform given by the second interval of data is opposite to that of the other two, so that the sum of the three Hilbert transforms is a single Hilbert transform. As a consequence, the reconstruction on the R-lines has three times more noise power than the reconstruction on the π-lines since the noise is additive.

Figure 10:
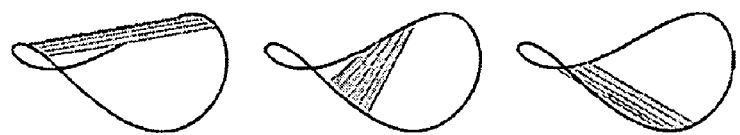
FIG. 10 illustrates three surfaces of R-lines for the saddle trajectory according to an embodiment of the present invention.

FIG. 10 illustrates three surfaces of R-lines for the saddle trajectory. The R-lines forming each of the three surfaces are parallel to a plane containing the z-axis. The angle between this plane and the x-axis is respectively 0, 45, and 90 degrees. The z-direction has been exaggerated in FIG. 10 for display purposes.

Saddle CB projections were simulated with and without Poisson noise. The added noise and the simulation parameters were the same as for the helical data, except that the value of P was 4.4 cm and the normal to the detector plane was chosen along the line joining the source position to the origin $\underline{x}=0$. From these projections, reconstructions were achieved on 300 surfaces of R-lines, three of which are illustrated in FIG. 10. The R-lines forming any given surface were parallel to a plane passing through the z-axis, and the 300 surfaces differed from each other in the angle between that plane and the x-axis, which varied uniformly from 0 to π.

Figure 11:
FIG. 11 illustrates reconstructions of the FORBILD head phantom without ears using embodiments of a method according to the present invention.

FIG. 11 illustrates reconstructions of the FORBILD head phantom without ears using embodiments of a method according to the present invention. Reconstructions with (right) and without (left) noise added to the data are shown. The top of FIG. 11 illustrates results on a surface of R-lines oriented at 45 degrees from the (x, z)-plane. The bottom of FIG. 11 illustrates results on the central sagittal slice created by interpolation of reconstructions on 300 R-line surfaces with angles with the (x, z)-plane uniformly distributed between 0 and π. The grayscale in FIG. 11 is: 0 to 100 HU.

FIG. 11 shows the reconstruction on the surface of R-lines at 45 degrees from the x-axis, and shows a reformatted slice at x=0 obtained on square pixels of side 0.075 cm using interpolation between the 300 reconstructions. As in the helical case, the accuracy of the results nicely supports the theory disclosed herein. Furthermore, it can be seen that there is no particular problem arising from the combination of reconstructions on different surfaces of R-lines. The average z distance between these surfaces was z=0.0577 cm and each surface of R-lines was parameterized using rotated (x, y) coordinates and discretized using square pixels of side 0.075 cm. The expected outcome of the reconstructions can be inferred from FIG. 7B. The inventors calculated that the R-line method produces here a reduction of 26% in axial extent of the required detector area, compared to the application of the first reconstruction step of the methods suggested in Katsevich or Chen or Pack-Noo-Kudo cited above. All reconstructions shown in this section assumed Ω to be a circular cylinder of radius 12.75 along the z-axis, and were performed using $\epsilon=0.2$ cm for inversion of the partial Hilbert transforms using the equations disclosed above.

The following is a discussion of reconstruction on measured lines (M-lines). Let E be the subset of points in $\Omega^+$ that belong to an R-line, and let an M-line be any measured line that intersects Ω and has the convex hull of its intersection with Ω included in E. By construction, an M-line need not be an R-line, and formula F2 gives a means to obtain samples of the Hilbert transform of $f$ on any M-line. Combining this means with the results disclosed above, a method is obtained to reconstruct $f$ on any M-line. Let $\underline{a}(\lambda)$ and $\underline{\alpha}$ be, respectively, the source position and the unit directional vector defining an M-line, and let $k(t,\underline{\alpha},\underline{a}(\lambda))$ and $K(t,\underline{\alpha},\underline{a}(\lambda))$ be respectively the expression for $f$ and its Hilbert transform on this line, following equations (2) and (3). Using this notation, the reconstruction method is described in the following four steps:

1) Determine the region $[t_{min}, t_{max}]$ that defines the convex hull of the intersection of the M-line with $\Omega$.

2) For each $t \in (t_{min}, t_{max})$, find source positions $\lambda^*_1$ and $\lambda^*_2$ that define the endpoints of the R-line through point $\underline{r}(t, \underline{\alpha}, \underline{a}(\lambda))$ on the M-line, see equation (1). By definition, $\lambda^*_1$ and $\lambda^*_2$ both depend on t, $\underline{\alpha}$ and $\lambda$, although the dependence is not written explicitly.

3) Use formula F2 to get the Hilbert transform of $f$ on the M-line for any $t \in (t_{min}, t_{max})$ i.e., compute $$K(t, \underline{\alpha}, \underline{a}(\lambda)) = -\frac{1}{2\pi}(b_a(\underline{r}(t, \underline{\alpha}, \underline{a}(\lambda)), \lambda, \lambda^*_1) + b_a(\underline{r}(t, \underline{\alpha}, \underline{a}(\lambda)), \lambda, \lambda^*_2)) \quad (51)$$

4) Apply equation (8) to obtain $k(t,\underline{\alpha},\underline{a}(\lambda))$ from $K(t,\underline{\alpha},\underline{a}(\lambda))$ for any $t \in (t_{min}, t_{max})$.

Note that equation (51) is simply a rewriting of equation (38) using $\lambda$ for $\lambda_3$, and using $\underline{r}(t,\underline{\alpha},\underline{a}(\lambda))$ for $\underline{x}$ following equation (6).

The above method defines a generalization of the R-line approach discussed previously. In comparison with the R-line approach, the M-line reconstruction is still limited to points in E, but there is now a degree of freedom in the selection of the line used for reconstruction at a given location $\underline{x}$ since this line need not be an R-line. Because the last reconstruction step is nonlocal, this degree of freedom increases imaging capabilities in the presence of truncation. For reconstruction on an M-line, we have the following data completeness condition:

Accurate reconstruction on an M-line through a given source position $\underline{a}$ is possible whenever each point $\underline{x}$ on the convex hull of the intersection of the M-line with $\Omega$ is visible while the source travels from $\underline{a}$ to both endpoints of an R-line through $\underline{x}$.

This condition differs from that for the R-line approach in that reconstruction at a given $\underline{x}$ no longer requires reconstruction to be possible at every point of the convex hull of the intersection of $\Omega$ and the R-line through $\underline{x}$. Thus, flexibility is added.

Consider again the truncation problem illustrated in FIG. 6 for HCBT. The inventors now that the added flexibility of the M-line method allows accurate reconstruction to be achieved in most of the FOV, which is a subset of E by property of the $\pi$-lines, see Danielsson et al. Let $\underline{x}$ be any point that has an (x, y) position within the shaded region of FIG. 6A. Geometrically, there always exists a $\pi$-line through this point and one source position between the endpoints of this $\pi$-line that has the same $\underline{x}$-coordinate as $\underline{x}$. Let $\underline{a}(\lambda^*)$ be that source position. Due to the location of $\underline{a}(\lambda^*)$, the M-line that goes through $\underline{x}$ from $\underline{a}(\lambda^*)$ has the convex hull of its intersection with $\Omega$ entirely included in the FOV. Furthermore, this M-line intersects the detector within the TD window. Hence, data within the transversely truncated TD window that covers the FOV of FIG. 6A is sufficient to reconstruct $f$ at any point that has an (x, y) position within the shaded region of FIG. 6A.

D. M-Line Simulations

The inventors have tested the above HCBT result on transverse truncation using computer simulated data of an intermittently truncated helical CB scan of an abdomen phantom described in Table I.

TABLE I

POPEYE PHANTOM DESCRIPTION

| Type | $x_c$ | $y_c$ | $z_c$ | a | b | c | θ | Density (HU) |
|---|---|---|---|---|---|---|---|---|
| C | 0 | 0 | 0 | 16.5 | 10 | 10 | 0 | 0 |
| C | −21 | 0 | 0 | 4.5 | 7 | 10 | 0 | 0 |
| C | 21 | 0 | 0 | 4.5 | 7 | 10 | 0 | 0 |
| C | −21 | 0 | 0 | 2 | 2 | 10 | 0 | 500 |
| C | −21 | 0 | 0 | 1.4 | 1.4 | 10 | 0 | 20 |
| C | 21 | 0 | 0 | 2 | 2 | 10 | 0 | 500 |
| C | 21 | 0 | 0 | 1.4 | 1.4 | 10 | 0 | 20 |
| E | −8.5 | −0.5 | 0 | 6 | 5 | 3.5 | −20 | 60 |
| E | −2.5 | 1.5 | 1 | 5 | 4 | 3.5 | 0 | 60 |
| E | −3 | 1.5 | 0 | 4.3 | 0.9 | 1.5 | 0 | 55 |
| E | 9 | 0.5 | 0 | 6 | 4.5 | 5 | −30 | 50 |
| E | 8 | 0.5 | 0 | 4 | 3.2 | 3.5 | −30 | 30 |
| E | 0.8 | 8 | −2.5 | 1.8 | 1.3 | 0.5 | 0 | 40 |
| E | 0.8 | 7 | 0 | 1.8 | 1.3 | 0.5 | 0 | 40 |
| E | 0.8 | 8 | 2.5 | 1.8 | 1.3 | 0.5 | 0 | 40 |
| C | 0 | −7.2 | −2 | 2 | 1.3 | 0.9 | 0 | 500 |
| C | 0 | −7.2 | −2 | 1 | 1 | 0.9 | 0 | 20 |
| C | 0 | −7.2 | −0.8 | 1 | 1 | 0.3 | 0 | 50 |
| C | 0 | −7.2 | 0.4 | 2 | 1.3 | 0.9 | 0 | 500 |
| C | 0 | −7.2 | 0.4 | 1 | 1 | 0.9 | 0 | 20 |
| C | 0 | −7.2 | 1.6 | 1 | 1 | 0.3 | 0 | 50 |
| C | 0 | −7.2 | 2.8 | 2 | 1.3 | 0.9 | 0 | 500 |
| C | 0 | −7.2 | 2.8 | 1 | 1 | 0.9 | 0 | 20 |
| C | 0 | −7.2 | 4 | 1 | 1 | 0.3 | 0 | 50 |
| C | 0 | −7.2 | 5.2 | 2 | 1.3 | 0.9 | 0 | 500 |
| C | 0 | −7.2 | 5.2 | 1 | 1 | 0.9 | 0 | 20 |
| E | 0 | −4 | 0 | 0.32 | 0.45 | 1.5 | 0 | 30 |
| E | 1 | −4 | 0 | 0.45 | 0.32 | 1.5 | 0 | 30 |

This phantom, dubbed the Popeye phantom, was specifically designed with low contrast abdomen structures and large arms to demonstrate the ability to handle transverse truncation. All parameters used for the experiment were identical to those used for the helical simulations of discussed above except that the number of photons used to simulated noisy data and P were increased to 500,000 and 7.4 cm, respectively. Also, the number of detector elements per row was only large enough to cover a cylindrical FOV of radius 13 cm while the radius needed to avoid transverse truncation with the Popeye phantom is 25.5 cm.

Figure 12:
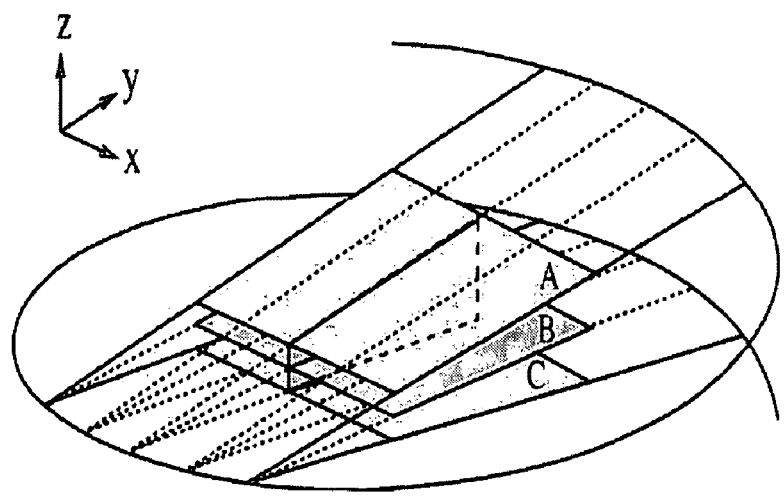
FIG. 12 illustrates a wedge volume where accurate reconstruction is possible over the FOV despite transverse truncation according to an embodiment of the present invention.

FIG. 12 illustrates a wedge volume where accurate reconstruction is possible over the FOV despite transverse truncation according to an embodiment of the present invention. Surfaces A and C are surfaces of $\pi$-lines, while surface B is a surface of M-lines that are not R-lines. The FOV can be covered using a stack of edges such as that displayed here. Hence, reconstruction from transversely truncated data is possible at any z in the FOV. Reconstruction was achieved on a wedge composed of M-line surfaces three of which are illustrated (though not to scale) in FIG. 12. Stacking several such wedges with alternating orientation (+y, −y, +y . . . ) allows full coverage of the FOV in the axial direction, see e.g., Tam et al. and Danielsson et al. The wedge was discretized into 55 M-line surfaces such that the axial distance between the central points on adjacent surfaces was 0.0685 cm. Notice that the top and bottom M-line surfaces (labeled A and C in FIG. 12) are $\pi$-line surfaces but the other 53 including the central one labeled B are not.

Figure 13:
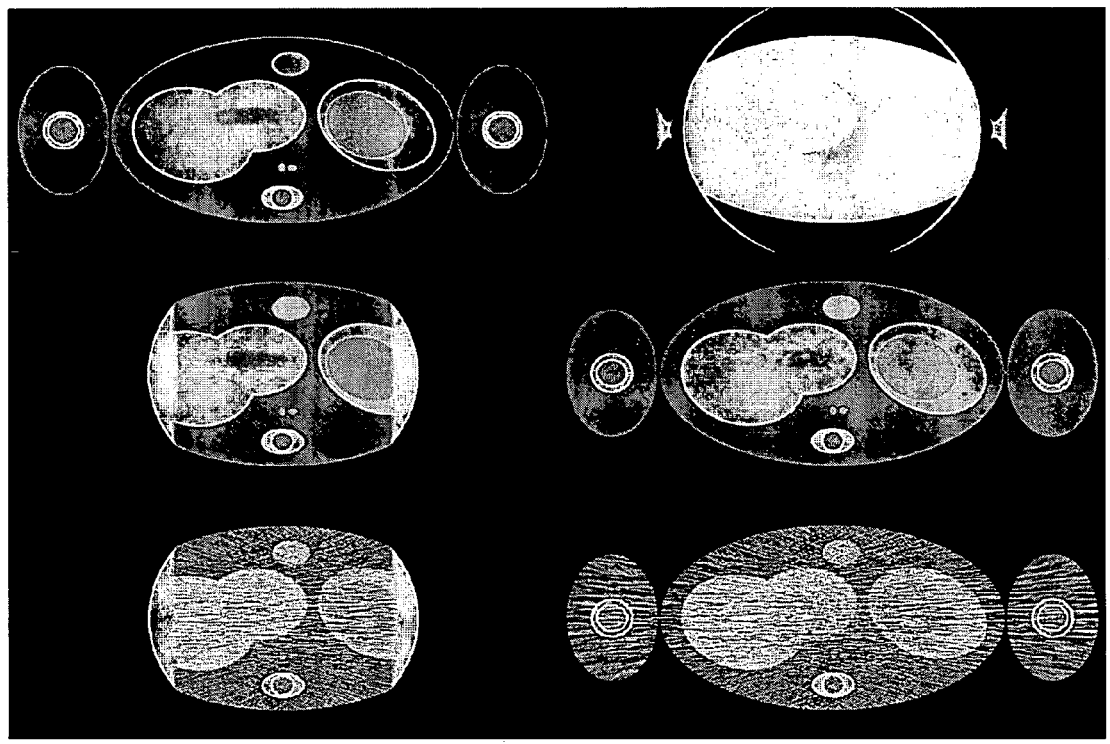
FIG. 13 is images representing the Popeye phantom on the central M-line surface within a wedge according to an embodiment of the present invention.

FIG. 13 is images representing the Popeye phantom on the central M-line surface within a wedge, see e.g., surface B in FIG. 12. The top row shown in FIG. 13 includes (left) original, (right) Katsevich reconstruction with transversely truncated data. The middle row shown in FIG. 13 includes (left) reconstruction from transversely truncated data using the Hilbert transform approach, (right) Katsevich reconstruction from nontruncated data. The bottom row shown in FIG. 13 includes same as middle row but with Poisson noise added to the data. The grayscale in FIG. 13 is −80 to 140 HU.

Figure 14:
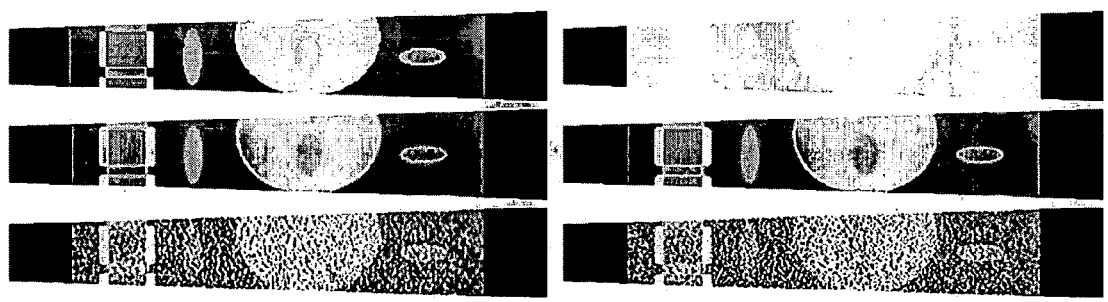
FIG. 14 is images representing the Popeye phantom on a central vertical slice within a wedge as illustrated in FIG. 12 according to an embodiment of the present invention.

FIG. 14 is images representing the Popeye phantom on a central vertical slice within a wedge as illustrated in FIG. 12. Top row: (left) original, (right) Katsevich reconstruction with transversely truncated data. Middle row: (left) reconstruction from transversely truncated data using the Hilbert transform approach, (right) Katsevich reconstruction from nontruncated data. Bottom row: same as middle row but with Poisson noise added to the data. The grayscale in FIG. 14 is −40 to 70 HU.

FIGS. 13 and 14 show a reconstruction on this central slice and on a central vertical slice also visible in FIG. 12, using a compressed grayscale (−40 to 70 HU). In both FIGS. 13 and 14, the upper left image is the original phantom (shown for reference), the upper right is the result of naively applying the prior art formula of Katsevich despite the presence of transverse truncation in the data, and the other two rows or images compare the results of the M-line method using truncated data (left) to those of the Katsevich formula using nontruncated data (right), without and with Poisson noise added to the data. Despite intermittent transverse truncation of the data, the images produced using the M-line method are in good agreement with those produced by applying the exact formula of Katsevich to nontruncated data. This observation is striking when one considers the implications for clinical CT that accompany it. Specifically, if we assume that the region of interest (ROI) can be appropriately positioned, radiation can be more narrowly collimated in the transverse direction leading to a reduction in the X-ray dose and in the likelihood that the patient will contract cancer as a result of the scan.

The following is another important application of the M-line method to HCBT. Given the new freedom that the M-line method affords with regard to the direction along which the Hilbert inversion is performed for reconstruction at a given location, it is natural to wonder what effect, if any, this choice has on the noise properties of the final reconstruction. In the case of a 180° 2-D parallel-beam scan, no significant difference is observed when the inversion is performed along lines parallel to the x-axis in stead of the y-axis, see e.g., Noo-Clackdoyle-Pack cited above. However, in HCBT with a third-generation multi-row detector the situation is different because redundant data is always available at pitch values that provide complete data, i.e., data outside the TD window is always measured, see e.g., Proksa et al. cited above and D. Heusher, K. Brown and F. Noo, "Redundant Data and Exact Helical Cone-Beam Reconstruction," *Phys, Med. Biol.*, Vol. 49, 2004. Such redundant data can be incorporated into the reconstruction by applying the M-line method to M-lines that fall outside the TD window.

Let $\lambda_{in}$ and $\lambda_{out}$ be the first and the last source position at which a given point $\underline{x}$ is visible. Assuming no transaxial truncation and a FOV radius and pitch P low enough to avoid interrupted illumination, $\underline{x}$ is visible for all $\lambda \in [\lambda_{in}, \lambda_{out}]$ and assuming the data is complete, the endpoints $\lambda_1$ and $\lambda_2$ of the π-line through $\underline{x}$ are such that $\lambda_{in} < \lambda_1 < \lambda_2 < \lambda_{out}$. Hence, reconstruction at $\underline{x}$ with the M-line method can be achieved using any M-line through $\underline{x}$ with $\lambda \in [\lambda_{in}, \lambda_{out}]$, and in particular $\lambda = \lambda_{in}$ and $\lambda = \lambda_{out}$, without introducing CB artifacts. Such nonapproximate incorporation of an arbitrary amount of redundant data in the reconstruction represents a novel achievement, but is only of value if it can improve noise performance. The fact that the use of redundant data in the π-window using the R-line method resulted in an increased noise level (FIG. 9) suggests that reconstructions using M-lines outside the TD window might have the same negative result. Experimental results shown in FIG. 15 confirm this suspicion. However, as discussed below, the average of reconstructions obtained from different M-lines can lead to a significant improvement in noise performance thanks to statistical differences that originate from the difference in the data involved for each reconstruction.

Figure 15:
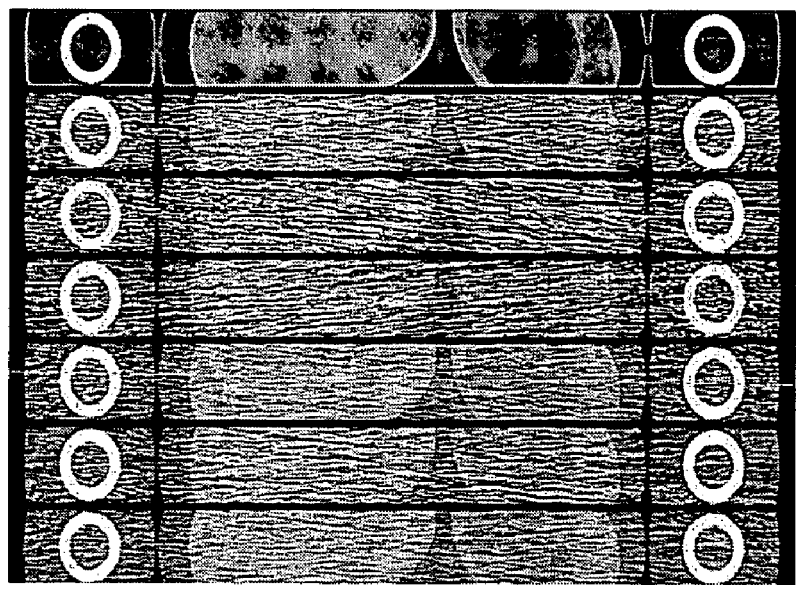
FIG. 15 illustrates various reconstructions of the 3-D Popeye phantom demonstrating the utilization of minimally redundant data for noise reduction according to an embodiment of the present invention.

FIG. 15 illustrates various reconstructions of the 3-D Popeye phantom demonstrating the utilization of minimally redundant data for noise reduction. The grayscale shown in FIG. 15 is −80 to 140 HU. The images in FIG. 15 represents the Popeye phantom on a (limited) set of π-lines parallel to the (x, z)-plane and similar to those of FIG. 6B. The top image in FIG. 15 is the original phantom while the remaining six images are reconstructions from simulated data with Poisson noise. All simulation and reconstruction parameters are identical to those used for the HCBT experiments discussed above except that the number of photons was increased to 500,000 and Ω was assumed to be a central cylinder of radius 26.4 cm. Also, the number of simulated detector rows was such that P was the maximum pitch for data completeness, which yields a data redundancy of about 30%, see Heuscher et al. The second through fourth images show the results obtained when the reconstruction at each point $\underline{x}$ is done by respectively applying the M-line method to three lines through $\underline{x}$, namely the π-line, the M-line through $\underline{a}(\lambda_{in})$ and the M-line through $\underline{a}(\lambda_{out})$. The fifth image is the average of the previous three images, the sixth is obtained by applying the formula of Katsevich, and the seventh is the average of images three, four and six. Table II, below, summarizes the total relative error in each image as well as that in each arm and in the central section.

TABLE II

RELATIVE ERRORS ON RECONSTRUCTIONS OF THE POPEYE PHANTOM

| Region | Full | Left-arm | Right-arm | Central |
|---|---|---|---|---|
| π-rcn | 6.7 | 7.8 | 7.6 | 6.0 |
| π⁻-rcn | 10.4 | 14.0 | 8.5 | 9.6 |
| π⁺-rcn | 10.5 | 8.9 | 14.0 | 9.7 |
| Aver. 1 | 4.8 | 5.7 | 5.7 | 4.2 |
| Kat. rcn | 5.6 | 5.4 | 5.4 | 5.8 |
| Aver. 2 | 4.7 | 5.3 | 5.5 | 4.2 |

The results of Table II and the images in FIG. 15 clearly demonstrate for the first time that (minimally) redundant data can be successfully used to reduce noise in HCBT without introduction of CB artifacts due to approximations in the reconstruction process.

The discussion in the previous section disregards trajectories that are formed from multiple smooth curves. If multiple source curves exist we can reconstruct using each one separately and merge the results. However, this approach is often too restrictive. For example, using the circle-plus-line trajectory of equation (18) we would only be able to reconstruct in the plane of the circle, while it is known that reconstruction over a much larger region is possible. See e.g., Tuy; Smith; and Noo-Clackdoyle-Defrise cited above. The following section extends the fundamental DBP equation (34) to a more general form in such a way that data from different source curves can be combined for reconstruction.

Figure 16A:
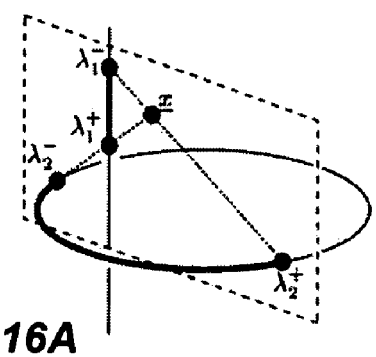
FIGS. 16A-D are illustrations of parameters involved in the extended DBP formula according to embodiments of the present invention.
Figure 16B:
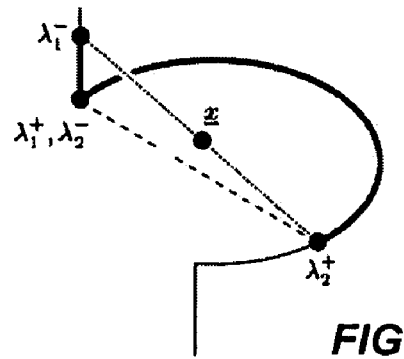
Figure 16C:
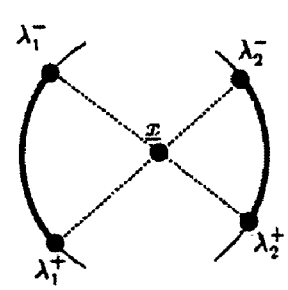
Figure 16D:
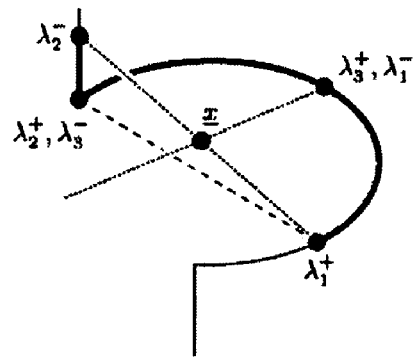

Consider a point $\underline{x} \in \Omega^+$ and P intervals of source positions, $[\lambda_p^-, \lambda_p^+]$, $p=1, \ldots P$, such that 1) each interval defines a segment of one of the N smooth curves forming the source trajectory and 2) for each $p=1, \ldots P-1$, either $\underline{a}(\lambda_p^+)=\underline{a}(\lambda_{p+1}^-)$ or the line connecting $\underline{a}(\lambda_p^+)$ to $\underline{a}(\lambda_{p+1}^-)$ passes through $\underline{x}$. FIGS. 16A-D illustrates this situation for three different source trajectories: 1) the circle-plus-line trajectory of equation (18), 2) two disconnected coplanar circle arcs, and 3) a "curl" trajectory that consists of a short-scan circular arc connected to two segments of line orthogonal to it. FIGS. 16A-D are illustrations of the parameters involved in the extended DBP formula according to embodiments of the present invention. More specifically, FIG. 16A illustrates the circle-plus-line trajectory with $\underline{x}$ above the circle and P=2. FIG. 16B illustrates the curl trajectory with $\underline{x}$ above the plane of the short-scan and P=2. FIG. 16C illustrates two arcs of a single circle with $\underline{x}$ between them in the same plane and P=2. FIG. 16D illustrates the curl trajectory with $\underline{x}$ above the plane of the short-scan and P=3. The extended DBP formula allows reconstruction at $\underline{x}$ except for the geometry of FIG. 16C.

Now, let $k_p = -1$ when $\underline{x}$ is between $\underline{a}(\lambda_p^+)$ and $\underline{a}(\lambda_{p+1}^-)$, and $k_p = 1$ otherwise, for $p=1, \ldots P-1$. Using these numbers and the equation (36) of the DBP with boundary terms, we have the following extended DBP formula for reconstruction at $\underline{x}$.

$$\frac{1}{\pi} \sum_{p=1}^{P} q_p b_a(\underline{x}, \lambda_p^-, \lambda_p^+) - q_P K^*(\underline{w}, (\lambda_P^+, \underline{x}), \underline{x}) - K^*(\underline{w}, (\lambda_1^-, \underline{x}), \underline{x}) \quad (52)$$

where $q_1 = 1$ and $$q_P = \prod_{r=1}^{p-1} k_r \text{ for } p > 1,$$

and where $\underline{\omega}(\lambda_1^-, \underline{x})$ and $\underline{\omega}(\lambda_p^+, \underline{x})$ are given by equation (35). This formula is easily proved from equation (34). Let LHS and RHS be, respectively, the left-hand and the right hand-sides of equation (52). From equation (34), we get $$\begin{aligned}
LHS &= \sum_{p=1}^{P} q_P \{ K^*(\underline{w}, (\lambda_p^+, \underline{x}), \underline{x}) - K^*(\underline{w}, (\lambda_p^-, \underline{x}), \underline{x}) \} \quad (53) \\
&= RHS + \sum_{p=1}^{P-1} q_P \{ K^*(\underline{w}, (\lambda_p^+, \underline{x}), \underline{x}) - k_p K^*(\underline{w}, (\lambda_{p+1}^-, \underline{x}), \underline{x}) \} \\
&= RHS
\end{aligned}$$

since $K^*(\underline{w}(\lambda_p^+, \underline{x}), \underline{x}) = K^*(\underline{w}(\lambda_{p+1}^-, \underline{x}), \underline{x})$ for $k_p = 1$ and $K^*(\underline{w}(\lambda_p^+, \underline{x}), \underline{x}) = -K^*(\underline{w}(\lambda_{p+1}^-, \underline{x}), \underline{x})$ for $k_p = -1$ due to $K^*$ being an odd function in its first argument.

As in the case of the nonextended DBP formula, we find the usefulness of equation (52) to be not at all obvious, except when $\underline{x}, \underline{a}(\lambda_1^-)$ and $\underline{a}(\lambda_p^+)$ are collinear. In that case, if $q_p = 1$ when $\underline{x}$ is between $\underline{a}(\lambda_1^-)$ and $\underline{a}(\lambda_p^+)$, the right-hand side of equation (52) becomes $2q_p K^*(\underline{w}(\lambda_p^+, \underline{x}), \underline{x})$, and equation (52) yields, therefore, a way to obtain a sample of the Hilbert transform of $f$ on the line through $\underline{a}(\lambda_p^+)$.

Going back to the examples of FIG. 16, the following illustrative observations can be made. In FIGS. 16A and 16B, P=2 and $q_2=1$ while $\underline{x}$ is between $\underline{a}(\lambda_1^-)$ and $\underline{a}(\lambda_2^+)$, therefore, equation (52) gives access to the Hilbert transform of F on the line from $\underline{a}(\lambda_1^-)$ and $\underline{a}(\lambda_2^+)$. In FIG. 16C, P=2 but $q_2 = -1$ while $\underline{x}$ is between $\underline{a}(\lambda_1^-)$ and $\underline{a}(\lambda_2^+)$, so equation (52) delivers nothing, in agreement with the understanding that the source trajectory is not complete for any reconstruction at $\underline{x}$. In FIG. 16D, P=3 and $q_3 = -1$, but $\underline{x}$ is not between $\underline{a}(\lambda_1^-)$ and $\underline{a}(\lambda_3^+)$, therefore, equation (52) gives access to the Hilbert transform of $f$ on the M-line that diverges from $\underline{a}(\lambda_3^+)$.

Basically, the extended DBP equation (52) allows us to build the Hilbert transform of $f$ on R-lines and M-lines that were not reachable when considering separately each smooth curve forming the source trajectory. In some cases, these lines are reached by combining data from disconnected source curves using R-lines to jump from one curve to another. In other cases, these lines are reached by just noting that corners in the segment of source trajectory that connects the end-points of an R-line are admissible in the DBP operation.

From a data completeness point of view, we note that reconstruction on an R-line or an M-line using equation (52) requires no more than the convex hull of the intersection of that line with $\Omega$ to be visible over the source trajectory. Hence, for such a reconstruction significant advantages are obtained in terms of data requirement over other previously published CB reconstruction methods. For example, in FIG. 16A, the reconstruction at $\underline{x}$ does not require data over the planes through $\underline{x}$ that do not intersect the circle, unlike the method in Noo-Clackdoyle-Defrise cited above, while allowing axial truncation. For another example, in FIG. 16B, the reconstruction on the R-line from $\underline{a}(\lambda_1^-)$ to $\underline{a}(\lambda_2^+)$ is possible from axially truncated projections, which is a completely original result.

The inventors have applied equation (52) to simulated projections of the FORBILD head phantom (without ears) on the curl trajectory of FIG. 16B. All applicable parameters from the experiments above were used in this experiment. The detector was wide enough to prevent transverse truncation, but not tall enough to prevent axial truncation. The short-scan arc covered 206 degrees with 696 source positions. Each line segment covered a distance of 5 cm with 25 source positions. Reconstruction was achieved on a surface of R-lines connecting point $\underline{a}(\lambda_1^-)$ of FIG. 16B (at 5 cm from the circular arc) to $\underline{a}(\lambda_2^+)$ with $(\lambda_2^+)$ spanning an arc of 52.8 degrees from the endpoint of the circular arc closest to the particular $\underline{a}(\lambda_2^+)$ in FIG. 16B. The distance between adjacent samples on each R-line was 0.075 cm and the angle between adjacent R-lines was chosen such that they intersected the short scan at points with an angular separation of 0.15 radians from the point of view at the center of the short scan.

Figure 17:
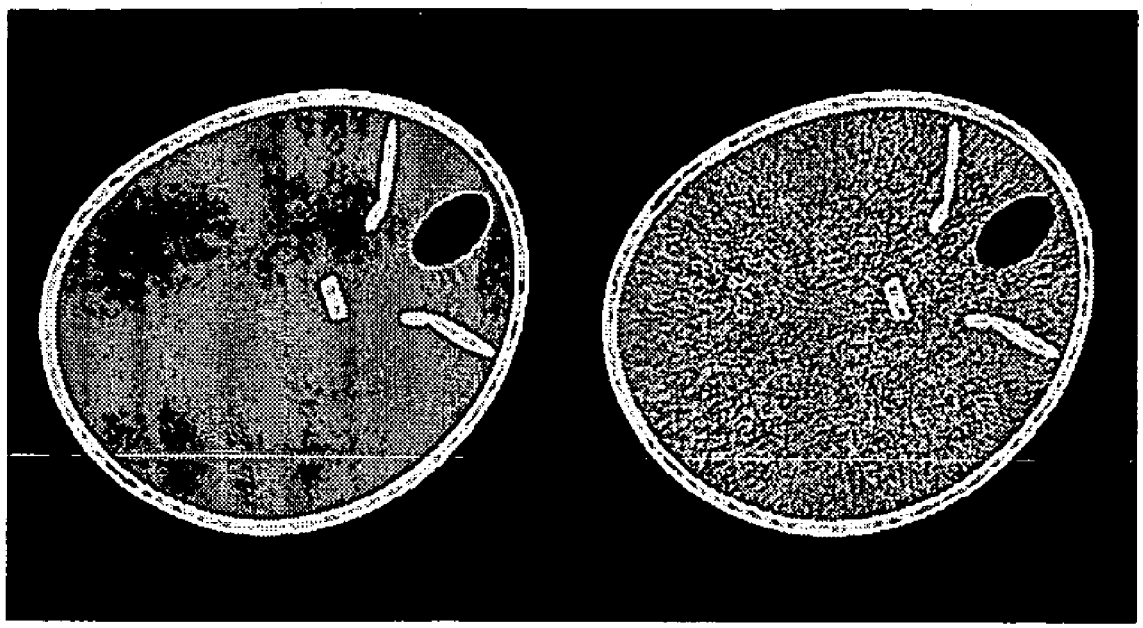
FIG. 17 illustrates reconstructions from simulated data using the extended DBP equation (52) without (left) and with (right) noise on a surface of R-lines according to embodiments of the present invention.

FIG. 17 illustrates reconstructions from simulated data using the extended DBP equation (52) without (left) and with (right) noise on a surface of R-lines. Each R-line was like the R-line from $(\lambda_1^-)$ to $(\lambda_2^+)$ in FIG. 16B. The surface was built by keeping $(\lambda_1^-)$ fixed and moving $(\lambda_2^+)$ counterclockwise from the extremity of the short-scan. The grayscale of FIG. 17 is 0 to 100 HU. The images in FIG. 17 show the reconstruction obtained with and without Poisson noise added to the data.

Figure 18:
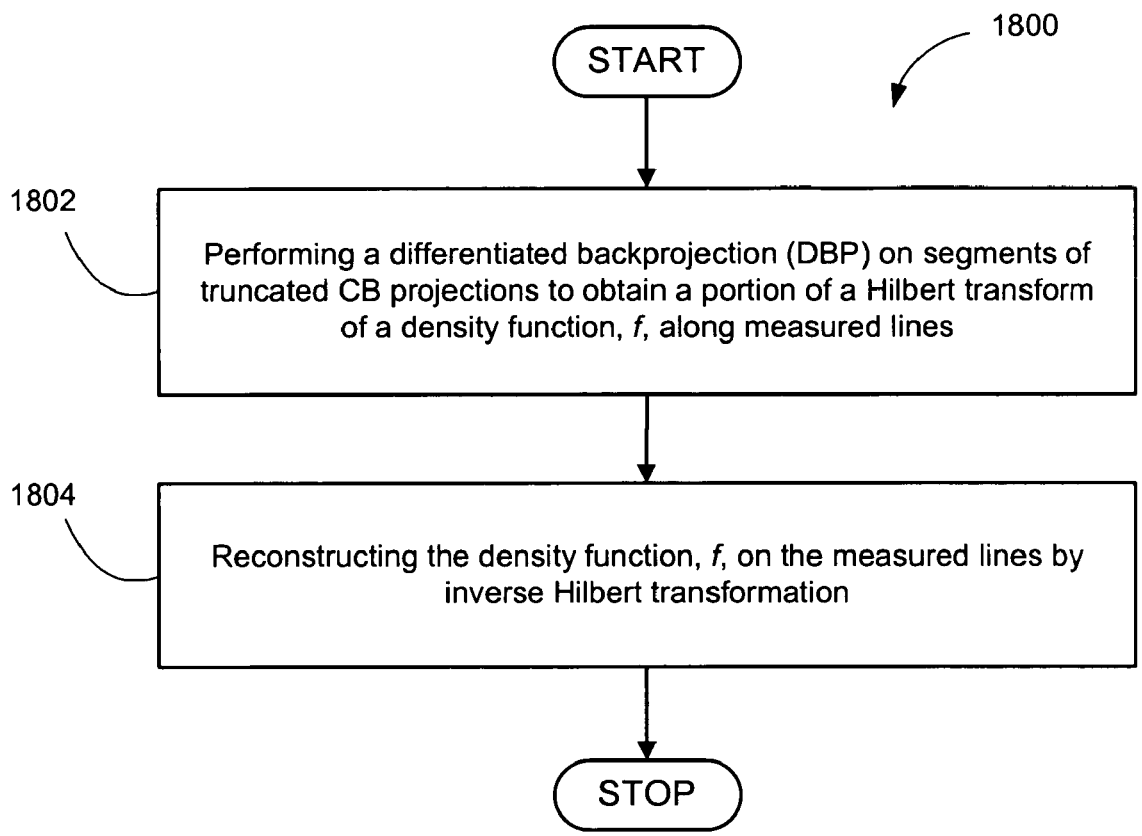
FIG. 18 is a flow chart of an embodiment of a method of CB reconstruction using truncated CB projections according to the present invention.

FIG. 18 is a flow chart of an embodiment of a method 1800 of CB reconstruction using truncated CB projections according to the present invention. Method 1800 may include performing 1802 a differentiated backprojection (DBP) on segments of truncated CB projections to obtain a portion of a Hilbert transform of a density function, $f$, along measured lines. Method 1800 may further include reconstructing 1804 the density function, $f$, on the measured lines by inverse Hilbert transformation. According to an embodiment of method 1800, the measured lines may be redundantly measured lines (R-lines). According to another embodiment of method 1800, performing 1802 a DBP on segments of the truncated CB projections, may include determining a region [$t_{min}$, $t_{max}$] that defines a convex hull of an intersection of an R-line with $\Omega$ and obtaining a Hilbert transform of the density function, $f$, on the R-line for any $t \in (t_{min}, t_{max})$. According to yet another embodiment of method 1800, obtaining a Hilbert transform of the density function, $f$, on the R-line for any $t \in (t_{min}, t_{max})$, may include computing:

$$K(t, \underline{\theta}_{12}, \underline{a}(\lambda_1)) = -\frac{1}{2\pi} b_a(\underline{r}, (t, \underline{\theta}_{12}, \underline{a}(\lambda_1)), \lambda_1, \lambda_2 \quad (48)$$

from the truncated CB projections for any $t \in (t_{min}, t_{max})$ where $\underline{r},(t,\underline{\theta}_{12},\underline{a}(\lambda_2))$ is the position vector on the R-line given by:

$$\underline{r}(t,\underline{\theta},\underline{s})=\underline{s}+t\underline{\theta}. \quad (1)$$

According to another embodiment of method 1800, reconstructing 1804 the density function, $f$ on the R-lines may include obtaining $k(t,\underline{\theta}_{12},\underline{a}(\lambda_1))$ from $K(t,\underline{\theta}_{12}, \underline{a}(\lambda_1))$ for any $t \in (t_{min},t_{max})$. According to another embodiment of method 1800, the measured lines may be M-lines. According to another embodiment of method 1800, performing a DBP on segments of the truncated CB projections may include determining a region [$t_{min}$, $t_{max}$] that defines a convex hull of an intersection of an M-line with $\Omega$. The embodiment of method 1800 may further include obtaining a Hilbert transform of the density function, $f$, on the M-line for any $t \in (t_{min}, t_{max})$. According to yet another embodiment of method 1800, obtaining a Hilbert transform of the density function, $f$, on the M-line for any $t \in (t_{min}, t_{max})$, may include for each $t \in (t_{min}, t_{max})$, finding source positions $\lambda^*_1$ and $\lambda^*_2$ that define endpoints of an R-line through point $\underline{r}(t,\underline{\alpha},\underline{a}(\lambda))$ on the M-line. The method 1800 may further include computing:

$$K(t, \underline{\alpha}, \underline{a}(\lambda)) = -\frac{1}{2\pi}(b_a(\underline{r}(t, \alpha, \underline{a}(\lambda)), \lambda, \lambda^*_1) + b_a(\underline{r}(t, \alpha, \underline{a}(\lambda)), \lambda, \lambda^*_2)). \quad (51)$$

According to another embodiment of method 1800, reconstructing the density function, $f$, on the M-lines may include obtaining $k(t,\underline{\alpha},\underline{a}(\lambda))$ from $K(t,\underline{\alpha},\underline{a}(\lambda))$ for any $t \in (t_{min},t_{max})$.

Figure 20:
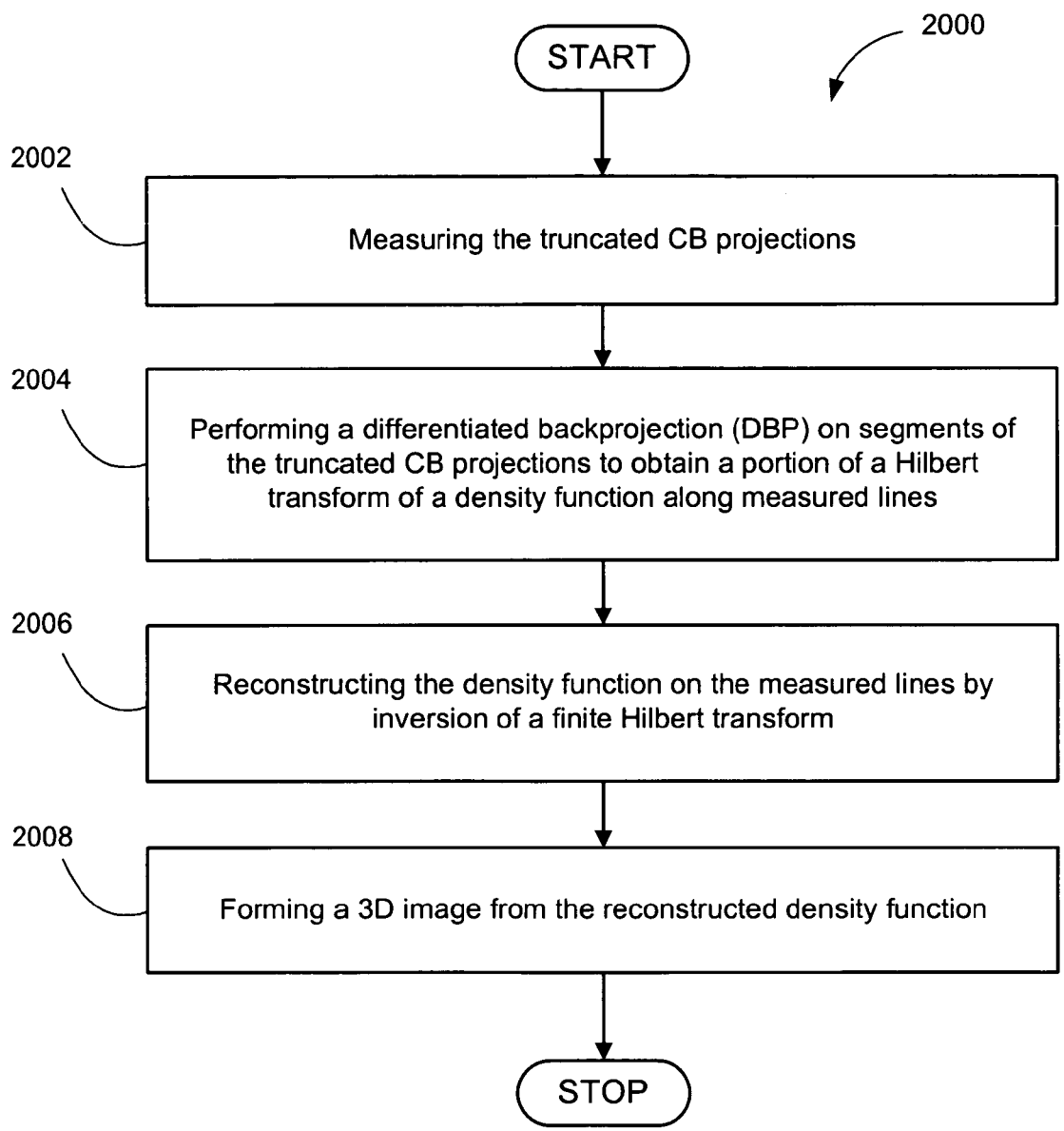
FIG. 20 is a flow chart of a method of image three-dimensional (3D) reconstruction from truncated cone-beam (CB) projections according to an embodiment of the present invention.

FIG. 20 is a flow chart of a method 2000 of image 3D reconstruction from truncated cone-beam (CB) projections according to an embodiment of the present invention. Method 2000 may include measuring 2002 the truncated CB projections. Method 2000 may further include performing 2004 a differentiated backprojection (DBP) on segments of the truncated CB projections to obtain a portion of a Hilbert transform of a density function along measured lines. Method 2000 may further include reconstructing 2006 the density function on the measured lines by inversion of a finite Hilbert transform. Method 2000 may further include forming 2008 a 3D image from the reconstructed density function.

Figure 19:
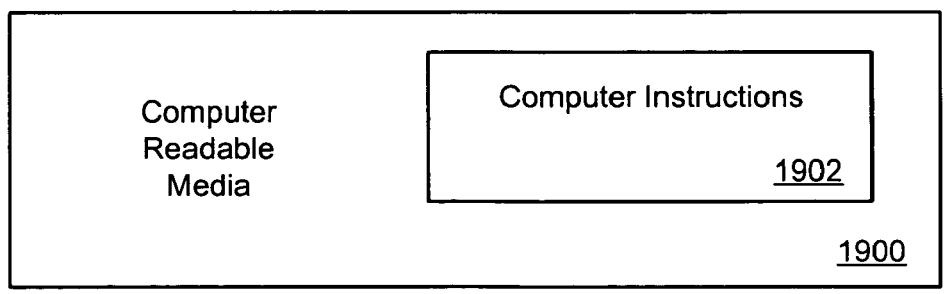
FIG. 19 is a block diagram of a computer readable media including computer readable instructions configured to implement methods according to embodiments of the present invention.

FIG. 19 is a block diagram of a computer readable media 1900 including computer readable instructions 1902 configured to implement methods 1800, 2000 according to embodiments of the present invention.

Figure 21:
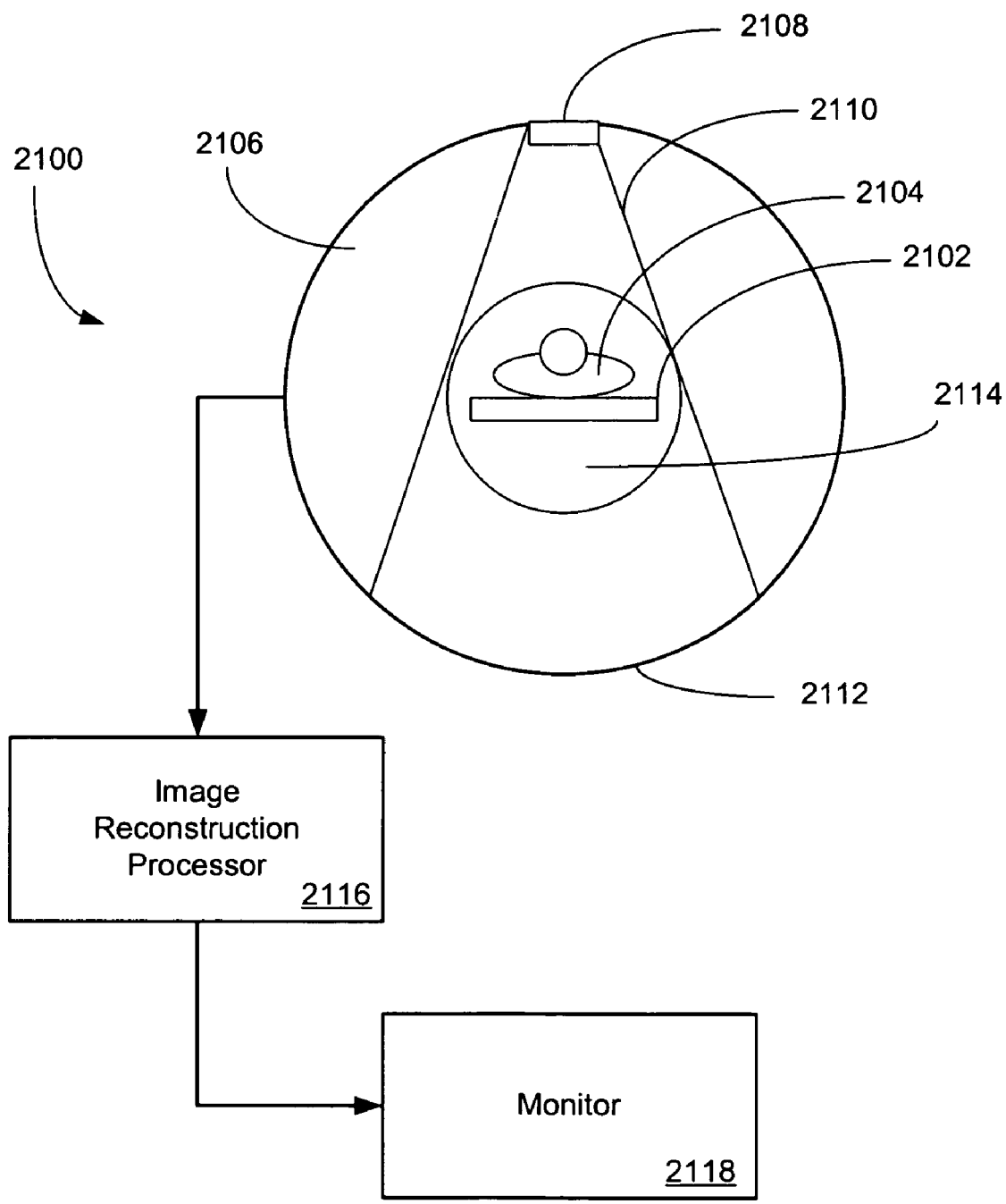
FIG. 21 is a block diagram of computed tomography (CT) scanner according to an embodiment of the present invention.

FIG. 21 is a block diagram of computed tomography (CT) scanner 2100 according to an embodiment of the present invention. CT scanner 2100 may include an object support 2102 configured for holding an object 2104 being examined at least partially within an examination region 2114. CT scanner 2100 may further include a rotating gantry 2106 surrounding the object support 2102 and configured for rotation about the examination region 2114. CT scanner 2100 may further include a source 2108 of penetrating radiation disposed on the rotating gantry 2106 for rotation therewith, the source 2108 of penetrating radiation emitting a cone-shaped beam 2110 of radiation that passes through the examination region 2114 as the rotating gantry 2106 rotates. CT scanner 2100 may further include an array 2112 of radiation detectors on the rotating gantry 2106 configured to receive cone-beam (CB) projections from the radiation emitted from the source 2108 of penetrating radiation after it has traversed the examination region 2114 the array 2112 further configured for a preselected data acquisition geometry. CT scanner 2100 may further include an image reconstruction processor 2116 for reconstructing images of the object 2104 from CB projections collected by the array 2112 of radiation detectors, the image reconstruction processor 2116 configured to implement method 1800 of CB reconstruction as described herein. CT scanner 2100 may further include a monitor 2118 in communication with the image reconstruction processor 2116 for viewing reconstructed images of the object 2104. According to additional embodiments of CT scanner 2100, the preselected data acquisition geometry may be any one of helix, saddle trajectories, or two-orthogonal-circle orbit.

In summary new methodology has been disclosed for accurate and stable reconstruction from CB projections obtained on a very general class of source trajectories. Compared to other reconstruction approaches, this methodology exhibits attractive features but also some drawbacks. Its key advantage is a low demand on detector coverage for reconstruction of a given ROI, which can be converted into increased imaging capabilities on a given system or into dose reduction techniques. Another advantage is its provision of an original means to incorporate redundant data into the reconstruction for the purpose of reducing data noise. Unfortunately, one necessary condition for reconstruction at a point $\underline{x}$ using this methodology is that $\underline{x}$ belong to an R-line. For some source trajectories, there are points that do not satisfy this condition, but do satisfy Tuy's condition. For example, consider the trajectory resulting from equation (50) if $2\lambda$ is replaced by $3\lambda$ in the definition of $\phi$. The convex hull of this trajectory, which is the region where Tuy's condition is satisfied, includes a central portion of the z-axis of length $PR/\sqrt{R^2+P^2}$. However, only one point on the z-axis belongs to an R-line, the point $\underline{x}$=0. Fortunately, there are many data acquisition geometries for which the region where Tuy's condition is satisfied is completely covered by R-lines. The list includes the helix, the newly introduced saddle trajectories, and even the two-orthogonal-circle orbit of Tuy.

As disclosed herein, several implementation strategies using our new methodology are possible for reconstruction with a given data acquisition geometry. These strategies differ in the choice of R-lines or M-lines over which the inversion is carried out and have to be tailored to the data acquisition to obtain an optimal reconstruction algorithm. Also, these strategies do not in general allow for reconstruction directly onto a 3-D rectilinear grid since the samples for the post-backprojection Hilbert inversion have to be on R-lines or M-lines. However, there are widely accepted reconstruction methods (such as AMPR) that also exhibit this feature, see e.g., T. Flohr, K. Stierstorfer, H. Bruder, J. Simon, A. Polacin and S. Schaller, "Image Reconstruction and Image Quality Evaluation for a 16-Slice CT Scanner," Med. Phys., Vol 30, No. 5, 2003.

The noise performance of embodiments of the new reconstruction methodology of the present invention was found to vary widely according to the implementation strategy. A comparison of the images in FIG. 9 demonstrated that reconstruction on a surface of R-lines that are not π-lines using an embodiment of the method of the present invention produces a higher noise level than that produced using Katsevich's formula (which is already not optimal in terms of noise). It is important to note, however, that these poor noise characteristics are not intrinsic to the methodology presented by this paper. In fact, the discussion herein demonstrated that in HCBT, reconstructing each point using the Hilbert transform along three different M-lines and averaging the results can significantly improve noise characteristics by incorporating data outside the TD window. Since current multi-slice CT scanners always have an amount of data in excess of the TD window, this ability constitutes a significant advance for HCBT.

The method of reconstruction on M-lines is remarkable in that it solves the intermittent transverse truncation problem in HCBT. This allows a smaller detector area to be used (and consequently a lower radiation dose to be delivered) for ROI imaging. Alternatively, wider patients can be accommodated on currently available clinical scanners. Note that this method of dealing with transverse truncation in HCBT can be as efficient as applying Katsevich's formula.

Finally, the inventors have observed that reconstruction from data acquired on a saddle trajectory can be achieved with the R-line reconstruction method using a significantly smaller detector than the methods of the prior art. In addition, the inventors have reason to believe that the R-line method is also more efficient, particularly in achieving high temporal resolution through the use of data from an appropriate limited segment of the saddle for each voxel.

While the foregoing advantages of the present invention are manifested in the detailed description and illustrated embodiments of the invention, a variety of changes can be made to the configuration, design and construction of the invention to achieve those advantages. Hence, reference herein to specific details of the structure and function of the present invention is by way of example only and not by way of limitation.

What is claimed is:

1. A method of computing an intermediate function for use in cone-beam (CB) reconstruction used to reconstruct 3D images, the intermediate function evaluated at a selected point in three dimensions where image reconstruction will be performed, the method comprising:
   obtaining CB projection data from a vertex path segment, wherein the vertex path segment comprises a path taken by an x-ray source in a reference frame of a target object to be reconstructed and wherein a chord connecting first and second endpoints of the vertex path segment does not include the selected point; and
   determining a difference between first and second values;
      the first value comprising a first Hilbert transform of a density function along a straight line passing through the first endpoint of the vertex path segment and the selected point, the first Hilbert transform evaluated at the selected point,
      the second value comprising a second Hilbert transform of the density function along a straight line passing through the second endpoint of the vertex path segment and the selected point, the second Hilbert transform evaluated at the selected point; and
   storing the difference values.

2. The method of claim 1, wherein the method further comprises computing a differentiated backprojection (DBP) of the CB projection data on the vertex path segment.

3. The method of claim 2, wherein the method further comprises determining a weighted average of first, second and third values;
   wherein the first value comprises an integral of the density function along a ray originating at the first endpoint of the vertex path segment and passing through the selected point;
   wherein the second value comprises a DBP of the CB projection data on the vertex path segment; and
   wherein the third value comprises an integral of the density function along a ray originating at the second endpoint of the vertex path segment and passing through the selected point.

4. A method of reconstructing an image from cone-beam (CB) projections acquired along a vertex path, the method comprising:
   selecting at least one image portion;
   for each image portion:
      selecting a series of points;
         for each point of the selected series of points:
            selecting at least one vertex path segment such that the point does not lie on a chord connecting a first endpoint and a second endpoint of any of the selected vertex path segments;
            for each of the selected vertex path segments: computing an intermediate function from CB projection data from the selected vertex path segment;
         using the computed intermediate functions to reconstruct a portion of the image; and
   reconstructing the image from the reconstructed portions of the image.

5. The method according to claim 4, further comprising storing the reconstructed image.

6. The method according to claim 5, wherein storing the reconstructed image comprises storing the reconstructed image on a computer readable medium.

7. The method according to claim 4, further comprising displaying the reconstructed image.

8. The method of claim 4, wherein each of the selected image portions is a line segment and wherein using the computed intermediate functions to reconstruct the selected image portion for each point on the selected line segment comprises:
   weighting the computed intermediate functions for each of the selected vertex path segments;
   adding the weighted, computed intermediate functions to produce a Hilbert transform of a density function along the line segment evaluated at the point; and
   inverting the Hilbert transform along the line segment to produce a reconstruction of the density function along the line segment.

9. A computed tomography (CT) scanner, comprising:
   an image reconstruction processor for reconstructing an image of an object from cone-beam (CB) projections acquired along a vertex path, the image reconstruction processor programmed to select at least one image portion and to select a series of points for each of the at least one image portion;
   for each point:
      selecting at least one vertex path segment such that the point does not lie on a chord connecting a first endpoint and a second endpoint of any of the selected vertex path segments;
      for each of the selected vertex path segments:
         computing an intermediate function from CB projection data from the selected vertex path segment;

using the computed intermediate functions to reconstruct a portion of the image; and reconstructing the image from the reconstructed portions of the image; and a monitor in communication with the image reconstruction processor for viewing the image.

10. The CT scanner according to claim 9, further comprising a computer readable medium in communication with the image reconstruction processor for storing the image.

11. The CT scanner according to claim 9, wherein each of the image portions selected by the image reconstruction processor is a line segment and wherein the image reconstruction processor further processes each of the points by:

weighting the computed intermediate functions for each of the selected at least one vertex path segments;

adding the weighted, computed intermediate functions to produce a Hilbert transform of a density function of the object along the line segment evaluated at the point; and inverting the Hilbert transform along the line segment to produce a reconstruction of the density function along the line segment.

12. The CT scanner according to claim 9, wherein the image reconstruction processor computes the intermediate function by:

evaluating the intermediate function at a selected point in three dimensions where image reconstruction will be performed;

obtaining CB projection data from a vertex path segment, wherein the vertex path segment comprises a path taken by an x-ray source in a reference frame of a target object to be reconstructed and wherein a chord connecting first and second endpoints of the vertex path segment does not include the selected point; and determining a difference between first and second values;

the first value comprising a first Hilbert transform of a density function along a straight line passing through the first endpoint of the vertex path segment and the selected point, the first Hilbert transform evaluated at the selected point, and the second value comprising a second Hilbert transform of the density function along a straight line passing through the second endpoint of the vertex path segment and the selected point, the second Hilbert transform evaluated at the selected point.

13. The CT scanner according to claim 12, wherein the image reconstruction processor further computes the intermediate function by computing a differentiated backprojection (DBP) of the CB projection data on the vertex path segment.

14. The CT scanner according to claim 13, wherein the image reconstruction processor further computes the intermediate function by determining a weighted average of first, second and third values:

the first value comprising an integral of the density function along a ray originating at the first endpoint of the vertex path segment and passing through the selected point;

the second value comprising a DBP of the CB projection data on the vertex path segment; and the third value comprising an integral of the density function along a ray originating at the second endpoint of the vertex path segment and passing through the selected point.

* * * * *

UNITED STATES PATENT AND TRADEMARK OFFICE
CERTIFICATE OF CORRECTION

| | | |
|---|---|---|
| PATENT NO. | : 7,477,720 B2 | Page 1 of 1 |
| APPLICATION NO. | : 11/371718 | |
| DATED | : January 13, 2009 | |
| INVENTOR(S) | : Jed Douglas Pack et al. | |

It is certified that error appears in the above-identified patent and that said Letters Patent is hereby corrected as shown below:

In the specification

In column 1, lines 19-24, replace "The U.S. Government has a paid-up license in this invention and the right in limited circumstances to require the patent owner to license others on reasonable terms as provided for in the terms of grants R21 EB000568 and R01 EB000621 awarded by the U.S. Department of Health and Human Services, National Institutes of Health (NIH)." with --This invention was made with government support under R21 EB000568 and R01 EB000627 awarded by the National Institutes of Health. The government has certain rights in this invention.--.

Signed and Sealed this
Sixteenth Day of February, 2016

Michelle K. Lee
*Director of the United States Patent and Trademark Office*